(12) United States Patent
Tegtmeier et al.

(10) Patent No.: US 7,732,437 B2
(45) Date of Patent: *Jun. 8, 2010

(54) USE OF ANTI-HISTAMINICS FOR ACUTE REDUCTION OF ELEVATED INTRACRANIAL PRESSURE

(75) Inventors: Frank Tegtmeier, Grevenbroich (DE); Frans Eduard Janssens, Bonheiden (BE); Joseph Elisabeth Leenaerts, Rijkevorsel (BE); Koenraad Arthur van Rossem, Vosselaar (BE); Manuel Jesús Alcázar-Vaca, Toledo (ES); Pedro Martínez-Jiménez, Madrid (ES); José Manuel Bartolomé-Nebreda, Toledo (ES); Antonio Gómez-Sánchez, Toledo (ES); Francisco Javier Fernández-Gadea, Toledo (ES); Jozef Leo Henri Van Reempts, Geel (BE)

(73) Assignee: Janssen Pharmaceutica, NV., Beerse (BE)

( * ) Notice: Subject to any disclaimer, the term of this patent is extended or adjusted under 35 U.S.C. 154(b) by 863 days.

This patent is subject to a terminal disclaimer.

(21) Appl. No.: 10/494,006

(22) PCT Filed: Nov. 22, 2002

(86) PCT No.: PCT/EP02/13180

§ 371 (c)(1),
(2), (4) Date: Apr. 28, 2004

(87) PCT Pub. No.: WO03/044023

PCT Pub. Date: May 30, 2003

(65) Prior Publication Data

US 2005/0070525 A1    Mar. 31, 2005

(30) Foreign Application Priority Data

Nov. 23, 2001   (EP)   ................................ 01204574

(51) Int. Cl.
*A61P 9/10* (2006.01)
*A61P 37/02* (2006.01)
*A61P 37/08* (2006.01)
*A61K 31/415* (2006.01)
*A61K 31/425* (2006.01)
*C07D 519/00* (2006.01)
*C07D 487/04* (2006.01)
*C07D 471/04* (2006.01)

(52) U.S. Cl. ................... 514/214.02; 540/578; 540/579
(58) Field of Classification Search ............ 514/214.02; 540/578, 579
See application file for complete search history.

(56) References Cited

U.S. PATENT DOCUMENTS 6,218,381 B1    4/2001   Janssens et al.
6,251,894 B1    6/2001   Janssens et al.
2004/0167138 A1*  8/2004   Janssens et al. ............. 514/269

FOREIGN PATENT DOCUMENTS

| EP | 0 675 889 | 10/1995 |
| WO | WO 94/13681 A1 | 6/1994 |
| WO | WO 97/24350 A1 | 7/1997 |
| WO | WO 97/34897 A1 | 9/1997 |
| WO | 1999/13871 A | 3/1999 |
| WO | 02/100862 A | 12/2002 |
| WO | WO 03/44023 A1 | 5/2003 |

OTHER PUBLICATIONS

Engelborghs, K., et al, *Temporal changes in intracranial pressure in a modified experimental model of closed head injury*, J. Neurosurg, 89: 796-806; 1998.

Engelborghs, K., et al., *Impaired autoregulation of cerebral blood flow in an experimental model of traumatic brain injury*, J. Neurotrauma, 17(8): 667-677, 2000.

Jain, K.K., Chapter 4: *Neuroprotection in Acute Trauma*, 'Neuroprotection in Cns Disorders: Commercial Opportunities'. A Jain PharmaBiotech Report: 65-73, 2000.

Mohanty, et al., *Journal of the Neurological Sciences*, 1989, 90:87-97.

(Continued)

*Primary Examiner*—Brenda L Coleman

(57) ABSTRACT

The invention concerns a novel histamine receptor antagonist and the use of an histamine receptor antagonist for the reduction of intracranial pressure (ICP), in particular for the prevention and treatment of elevated intracranial pressure and/or secondary ischaemida, in particular caused by brain injury, more in particular caused by traumatic (TBI) and non-traumatic brain injury. The novel compounds comprise compounds according to the general Formula (I) the pharmaceutically acceptable acid or base addition salts thereof, the stereochemically isomeric forms thereof and the N-oxide form thereof. In particular, the preferred compound is 3-[2-[4-(11,12-dihydro-6H-benzimidazo[2,1-b][3]benzazepin-6-yl)-2-(phenyl-methyl)-1-piperidinyl]ethyl]-2,10-dimethyl pyrimido[1,2-α]benzimidazol-4(10H)-one, the pharmaceutically acceptable acid or base addition salts thereof, the stereochemically isomeric forms thereof and the N-oxide form thereof. Also claimed is the novel use of commercially available histamine H1-and H2-receptor antagonists for the reduction of intracranial pressure (ICP).

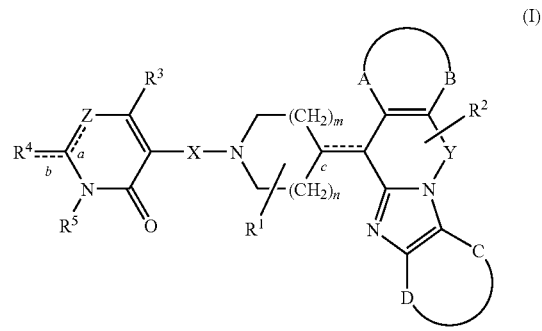

(I)

8 Claims, 4 Drawing Sheets

OTHER PUBLICATIONS

Stella, V.J., et al., "Prodrugs: the control of drug delivery via bioreversible chemical modification", 1980, pp. 112-176,.

Stella, V.J., et al., "Prodrugs: Do They Have Advantages in Clinical Practice?" 1985, 29: pp. 455-473.

Van Rossem, K., et al, *Brain oxygenation after experimental closed head injury, Adv. Exp. Med. Biol.* 471: 209-215, 1999.

Hungarian Novelty Search Report for corresponding Application No. HUP0402357.

Letter dated Oct. 8, 2009 regarding Hungarian Search Report.

International Search Report mailed Mar. 5, 2003,for corresponding Application No. PCT/EP02/13180.

* cited by examiner

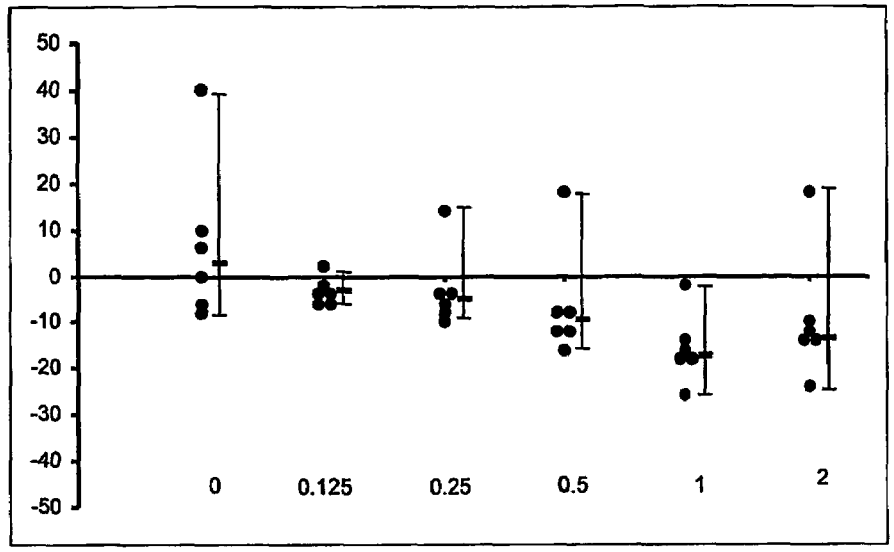

Figure 1. Dose dependence of the ICP reducing effect of Compound 2 during a 10 min infusion period. X-axis : Dose (mg/kg/min) ; Y-axis : Change in ICP as percentage of initial value.

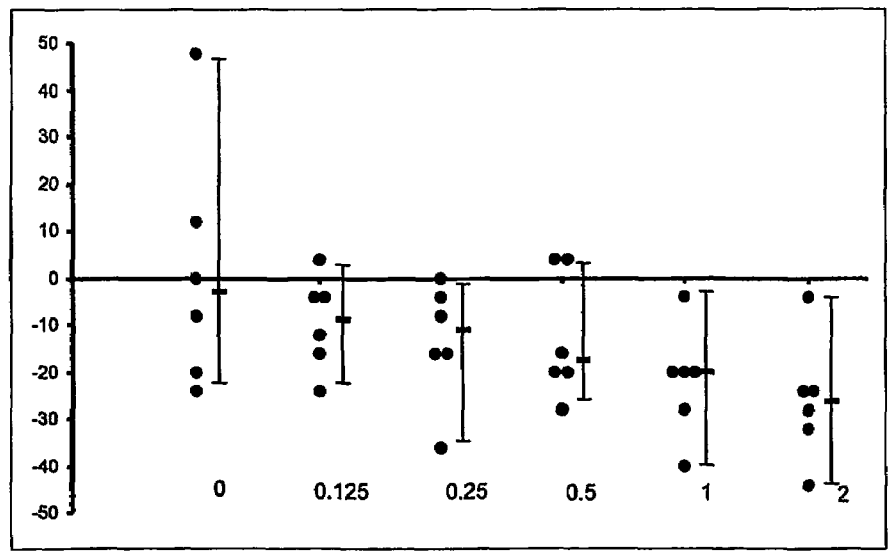

Figure 2. Dose dependence of the ICP reducing effect of Compound 2 during the 10 min post-treatment period following a 10 min infusion.
X-axis : Dose (mg/kg/min) ; Y-axis : Change in ICP as percentage of initial value.

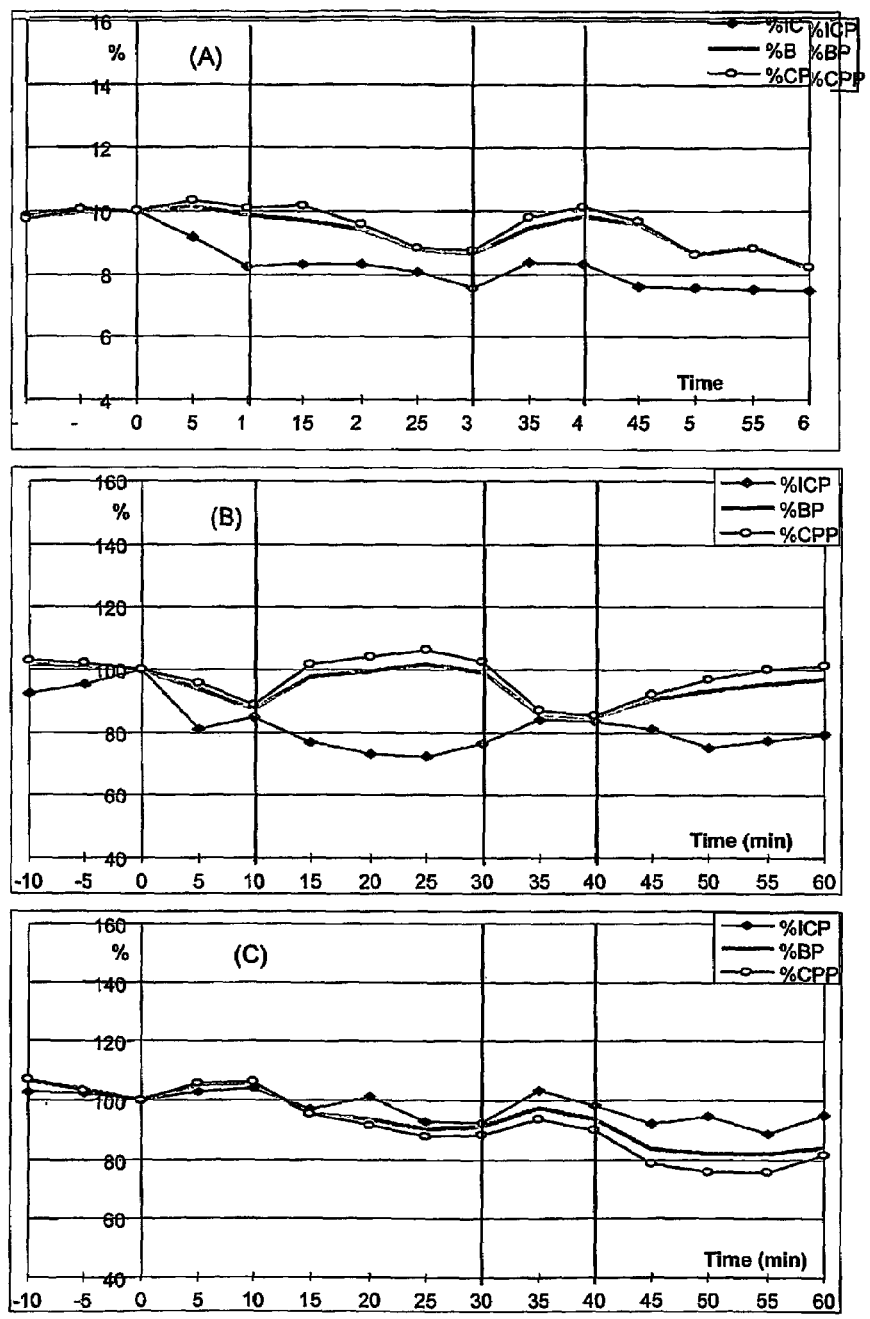

Figure 3: Time course of ICP, MABP and CPP in rats during 3 intermittent treatment periods of 10 min with respectively mannitol (Figure 3-A)(dose: 0.125 g/kg/min), Compound 2 (Figure 3-B) (dose: 1 mg/kg/min) and solvent (Figure 3-C)(10 % HP-beta-CD, pH 4). Treatment was started at 20 min after severe head injury (time = 0) and was repeated at 30 min and 60 min. The curves connect the median value for the subsequent time points. Values are expressed as % of initial value.

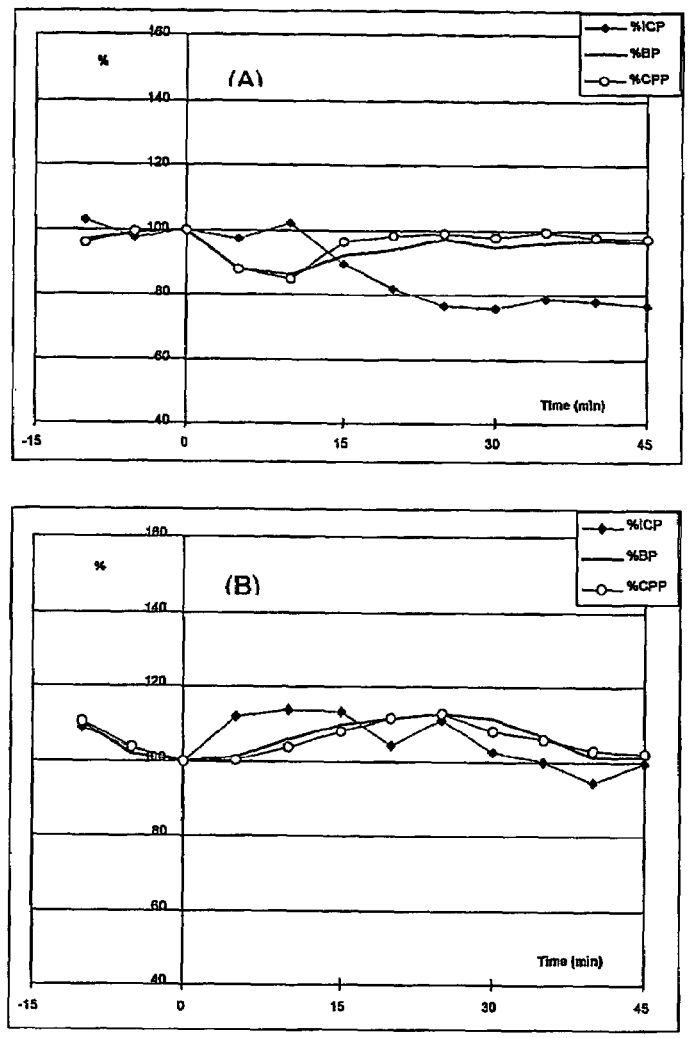
Figure 4: Time course of ICP, MABP and CPP in rabbits treated respectively with Compound 2 (Figure 4-A)(dose: 2 mg/kg/min during 10 min) or solvent (Figure 4-B)(2ml/min during 10 min). Treatment was started at 24 h after induction of a cortical cold lesion (time = 0). The curves connect the median value for the subsequent time points. Values are expressed as % of initial value.

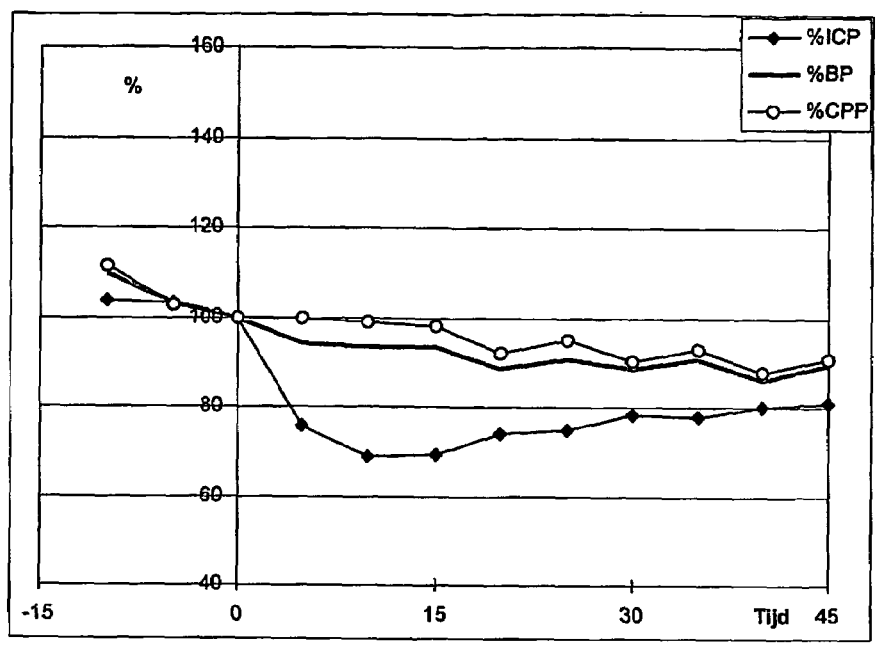
Figure 5 : Time course of ICP, BP and CPP in rabbits (m=6) treated with Pyrilamine (dose: 5 mg/kg/min during 10 min). The curves connect the median value for the subsequent time points. Values are expressed as % of initial value.

USE OF ANTI-HISTAMINICS FOR ACUTE REDUCTION OF ELEVATED INTRACRANIAL PRESSURE

CROSS REFERENCE TO RELATED APPLICATIONS

This application is the national stage of Application No. PCT/EP02/13180, filed Nov. 22, 2002, which application claims priority from EP 01204574.6 filed Nov. 23, 2001.

The invention concerns a novel histamine receptor antagonist and the use of an histamine receptor antagonist for the reduction of intracranial pressure (ICP), in particular for the prevention and treatment of elevated intracranial pressure and/or secondary ischaemia, in particular caused by brain injury, more in particular caused by traumatic (TBI) and non-traumatic brain injury.

TBI is a significant problem in developed countries. In the USA each year about 500,000 head injuries are severe enough to require hospitalisation. Mortality is high and approximately 80,000 of these TBI-patients face a life-long debilitating loss of function, 5,000 develop epilepsy and 2,000 live in a persistent vegetative state. TBI is the leading cause of death and disability in young adults today at an estimated cost in 1989 of over $25 billion per year.

Primary irreversible damage after brain trauma includes hemorrhage, contusion, neuronal necrosis and diffuse axonal injury. This damage, together with possible cardiovascular and respiratory depression, can induce acute secondary features including edema (vasogenic and/or cellular), secondary bleeding, alterations of cerebral blood volume (CBV), disturbed autoregulation of cerebral blood flow (CBF) and ischaemia. Edema, bleeding and an increase of CBV will increase the total brain volume and consequently the intracranial pressure (ICP). This in turn can lead to further progression of ischaemia, infarction, and, in severe cases, herniation of the brain stem with possible acute respiratory depression and death. Therapy in TBI should therefore be directed to the interruption of the pathologic cascade and the reduction of the brain volume and ICP. Prevention of a life threatening secondary increase in ICP, which often occurs e.g. in the post-acute phase after trauma or after cardiac resuscitation, is also a target for pharmacological treatment.

At present, the clinical tools for ICP reduction are limited. Standard treatment schedules include surgical drainage of the ventricles, blood pressure management, mannitol infusion, hyperventilation and high dose barbiturate therapy. Side effects of the non-surgical treatments include brain ischaemia, rebound effects on ICP and an increased risk for bacterial infections and sepsis. Also, various compounds with different mechanisms of actions (e.g. bradykinin antagonism, calcium antagonism, oxidative stress inhibition, glutamate receptor blockade and anti-epilepsy) have been tested in phase II and III clinical trials or are still under investigation (focus on outcome, not on ICP). Up to date no compound has been approved for the acute treatment of intracranial pressure (K. K. Jain, Chapter 4: Neuroprotection in Acute Trauma, 'Neuroprotection in CNS Disorders: Commercial Opportunities'. A Jain PharmaBiotech Report: 65-73, 2000). Obviously, there is a need for pharmaceuticals and/or therapies for the treatment of elevated intracranial pressure (ICP) and/or secondary ischaemia, in particular caused by brain injury, more in particular caused by traumatic brain injury (TBI).

SUMMARY OF THE INVENTION

The inventors have now found that substituted tetracyclic imidazole derivatives according to the general Formula (I) show histamine H1- and/or H2-receptor antagonist activity. Furthermore, the compounds have been shown to be particular useful for the reduction of intracranial pressure (ICP), in particular for the prevention and treatment of elevated intracranial pressure and/or secondary ischaemia, in particular caused by brain injury, more in particular caused by traumatic (TBI) and non-traumatic brain injury.

BRIEF DESCRIPTION OF THE DRAWINGS

FIG. 1. Dose dependence of the ICP reducing effect of compound 2 during a 10 min infusion period. X-axis : Dose (mg/kg/min) ; Y-axis : Change in ICP as percentage of initial value.

FIG. 2. Dose dependence of the ICP reducing effect of Compound 2 during the 10 min post-treatment period following a 10 min infusion. X-axis : Dose (mg/kg/min) ; Y-axis : Change in ICP as percentage of initial value.

FIG. 3: Time course of ICP, MABP and CPP in rats during 3 intermittent treatment periods of 10 min with respectively mannitol (FIG. 3-A)(dose: 0.125 g/kg/min), Compound 2 (FIG. 3-B) (dose: 1 mg/kg/min) and solvent (FIG. 3-C)(10 % HP-beta-CD, pH 4). Treatment was started at 20 min after severe head injury (time=0) and was repeated at 30 min and 60 min. The curves connect the median value for the subsequent time points. Values are expressed as % of initial value.

FIG. 4: Time course of ICP, MABP and CPP in rabbits treated respectively with Compound 2 (FIG. 4-A)(dose: 2 mg/kg/min during 10 min) or solvent (FIG. 4-B) (2ml/min during 10 min). Treatment was started at 24 after induction of a cortical cold lesion (time=0). The curves connect the median value for the subsequent time points. Values are expressed as % of initial value.

FIG. 5 : Time course of ICP, BP and CPP in rabbits (m=6) treated with Pyrilamine (dose: 5 mg/kg/min during 10 min). The curves connect the median value for the subsequent time points. Values are expressed as % of initial value.

DETAILED DESCRIPTION OF THE INVENTION

Furthermore, the inventors have found that compounds that antagonize the histamine H1- and/or H12-receptors (commonly called anti-histaminics) are also usefull for the reduction of intracranial pressure (ICP), in particular for the prevention and treatment of elevated intracranial pressure and/or secondary ischaemia, in particular caused by brain injury, more in particular caused by traumatic (TBI) and non-traumatic brain injury.

Characteristical to all compounds is that they are able to acutely reduce the intracranial pressure when administered to the bloodstream of a mammal, in particular by intraveneous administration Advantageously and very important, said compounds reduce the ICP while having little or no effect on the blood pressure, in particular a blood pressure-lowering effect, which is a most desired property of a potential drug. Hithertoo, histamine H1- and/or H2-receptor antagonists have not been developed for lowering the ICP, in particular for post-traumatic lowering of the ICP. Mohanty et al. in *Journal of the Neurological Sciences* 1989, 90:87-97 observed that histamine played a role in the forming of traumaticaly induced brain edema Increased brain water content and elevated plasma and brain histamine levels were prevented by prior treatment with the histamine H2-receptor antagonist cimetidine. However, meypyramine (an histamine H1-receptor antagonist) failed to reduce the increased brain water content and the histamine levels in the plasma and brain remained high. The effect on the ICP, in particular the action of histamine antagonists after a rise of the ICP for acutely reducing an increased ICP was not researched nor was the effect on the blood pressure.

Without being restricted theretoo, it is the opinion of the inventors tat, in view of the fact that the histamine receptor antagonists show the ability to reduce a normal ICP in the absence of brain edema and in view of the fact that the histamine receptor antagonists do not or only marginally influence the blood pressure, an effect attributed to peripheral vasodilatation, the mechanism of action is not one that acts purely on the reduction of brain edema nor via vasodilation, effects which are known in the prior art to occur for anti-histaminics.

Hence, the purpose of the present invention is to provide a substituted tetracyclic imidazole derivatives for use as an histmine antagonist, in particular as an histamine H1-antagonist, more in particular as an antagonist showing both histamine H1- and H2-antagonist activity, according to the general Formula (I)

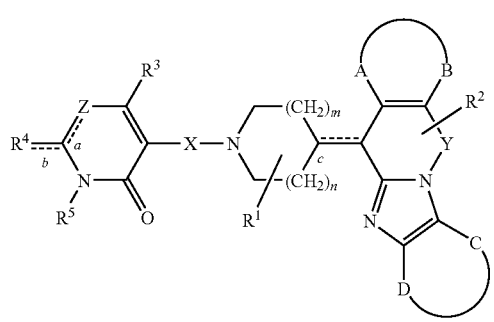

(I)

the pharmaceutically acceptable acid or base addition salts thereof, the stereochemically isomeric forms thereof and the N-oxide form thereof, wherein:

m is 1 or 2;

n is 0, 1 or 2;

a, b, c independently are a single or a double bond;

X is a covalent bond or a bivalent $C_{1-6}$alkanediyl radical wherein one or more —$CH_2$— groups may be optionally replaced with —O—, —S—, —CO—, or —$NR^7$— wherein:

$R^7$ is hydrogen, alkyl, Ar, Ar-alkyl, Het, Het-alkyl, hydroxyalkyl, alkyloxy, alkyloxyalkyl, alkyloxyalkyloxyalkyl, aminoalkyl, mono- or dialkylaminoalkyl, formyl, alkylcarbonylaminoalkyl, alkylcarbonyloxyalkcyl, alkyloxycarbonyl, alkyloxycarbonylalkyl, alkylaminocarbonyl, allylaminocarbonylalkyl, hydroxyalkyloxyalkyl, aminocarbonyl, aminocarbonylalkyl, alkyloxycarbonyl or alkylcarbonyloxyalkyloxyalkyl;

Y is a bivalent $C_{1-4}$alkanediyl or $C_{2-4}$ alkenediyl radical;

Z is N, in which case a is a double bond and b is a single bond or N—$R^7$ in which case a is a single bond, b is a double bond and $R^7$ is defined as above;

$R^1$, $R^2$ independently are hydrogen, hydroxy, alkyl, alkyloxy, Ar, Ar-alkyl, di(Ar-)alkyl, Het or Het-alkyl;

-A-B— independently is a bivalent radical of formula

-E-$CR^8$=$CR^8$— (a-1);

—$CR^8$=$CR^8$-E- (a-2);

—$CR^8$=$CR^8$—$CR^8$=CR— (a-3);

wherein $R^8$ each independently is hydrogen, halo, hydroxy, alkyl or alkyloxy;

E is a bivalent radical of formula —O—, —S— or —$NR^7$— wherein $R^7$ is defined as above;

—C-D- independently is a bivalent radical of formula

—$CR^8$=$CR^8$—$CR^8$=$CR^8$— (b-1);

—N=$CR^8$—$CR^8$=$CR^8$— (b-2)

—$CR^8$=N—$CR^8$=$CR^8$— (b-3)

—$CR^8$=$CR^8$—N=$CR^8$— (b-4);

—$CR^8$=$CR^8$—$CR^8$=N— (b-5)

wherein $R^8$ is defined as above;

$R^3$ is hydrogen, halo, hydroxy, alkyl, alkyloxy, Ar, Ar-alkyl, di(Ar-)alkyl, Het or Het-alkyl;

$R^4$ is hydrogen, alkyl, amino, alkylamino, Ar-amino, Het-amino, alkylcarbonylamino, Ar-carbonylamino, Het-carbonylamino, alkylaminocarbonylamino, Ar-aminocarbonylamino, Het-aminocarbonylamino, alkyloxyalkylamino, Ar-oxyalkylamino or Het-oxyalkylamino;

$R^5$ is hydrogen or alkyl;

or $R^4$ and $R^5$ together may form a bivalent radical of Formula

-M—$CR^9$=$CR^{10}$— (c-1);

—$CR^{10}$=$CR^9$-M- (c-2);

-M—$CR^9R^8$—$CR^{10}R^8$— (c-3);

—$CR^{10}R^8$—$CR^9R^8$-M- (c-4);

—$CR^8$=N—$NR^7$— (c-5);

—$NR^7$—N=$CR^8$— (c-6);

—$CR^8$=$CR^9$—$CR^{10}$=$CR^8$— (c-7);

—$CR^8R^8$—$CR^9R^8$—$CR^{10}R^8$-M- (c-8);

-M—$CR^{10}R^8$—$CR^9R^8$—$CR^8R^8$— (c-9);

—$CR^8R^8$—$CR^8$=N—$NR^7$— (c-10);

—$NR^7$—N=$CR^8$—$CR^8R^8$— (c-11);

wherein $R^7$ and $R^8$ are defined as above;

$R^9$, $R^{10}$ independently are hydrogen, alkyl, halo, haloalkyl; or $R^9$ and $R^{10}$ together may form a bivalent radical of formula —$CR^8$=$CR^8$—$CR^8$=$CR^8$—; and M is a bivalent radical of formula —$CH_2$—, —O—, —S— or —$NR^7$— wherein $R^7$ is defined as above.

In the framework of this application, Ar is a homocycle selected from the group of naphthyl and phenyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl and mono- or dialkylaminocarbonyl. Preferably, Ar is a naphthyl or phenyl, each optionally substituted with 1 substituent, each substituent independently selected from the group of halo or alkyl.

In the framework of this application, Het is a monocyclic heterocycle selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom with halo, hydroxy, alkyl or alkyloxy. Preferably, Het is pyridinyl, pyrazinyl or indolyl.

In the framework of this application, alkyl is a straight or branched saturated hydrocarbon radical having from 1 to 6 carbon atoms ; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms ; wherein each carbon atom can be optionally substituted with halo, hydroxy, alkyloxy or oxo. Preferably, alkyl is methyl, ethyl or cyclohexylmethyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms. Preferably, halo is fluoro or chloro and preferably, haloalkyl is trifluoromethyl.

A preferred group of compounds are those compounds according to Formula (I), the pharmaceutically acceptable acid or base addition salts thereof, the stereochemically isomeric forms thereof and the N-oxide form thereof, in which
-A-B— is a bivalent radical of formula (a-1) or (a-3), wherein E is a bivalent radical of formula —O—, —S— or —$NR^7$— wherein $R^7$ is hydrogen, $R^8$ is hydrogen, —C-D- is a bivalent radical of formula (b-1) or (b-2), wherein $R^8$ is hydrogen and Y is a bivalent radical of formula —$CH_2$—, —$CH_2$—$CH_2$— or —CH═CH—.

Another group of preferred compounds of Formula (I) are those compounds according to Formula (I), the pharmaceutically acceptable acid or base addition salts thereof, the stereochemically isomeric forms thereof and the N-oxide form thereof, in which m and n are both 1.

Another group of preferred compounds of Formula (I) are those compounds according to Formula (I), the pharmaceutically acceptable acid or base addition salts thereof, the stereochemically isomeric forms thereof and the N-oxide form thereof, in which $R^1$ and $R^2$, each independently are hydrogen, alkyl, Ar-alkyl, Het or Het-alkyl.

Yet another group of preferred compounds of Formula (I) are those compounds according to Formula (I), the pharmaceutically acceptable acid or base addition salts thereof, the stereochemically isomeric forms thereof and the N-oxide form thereof, in which X is a bivalent radical of formula —$CH_2CH_2$— or —$CH_2CH_2CH_2$—.

Yet another group of preferred compounds of Formula (I) are those compounds according to Formula (I), the pharmaceutically acceptable acid or base addition salts thereof, the stereochemically isomeric forms thereof and the N-oxide form thereof, in which $R^3$ is hydrogen or alkyl, Z is N—$R^7$ wherein $R^7$ is hydrogen or alkyl, a is a single bond and b is a double bond, and $R^4$ and $R^5$ together form a bivalent radical of Formula (c-1), (c-3), (c-5), (c-7), (c-8) or (c-10) wherein $R^7$ and $R^8$ are hydrogen.

Yet another group of preferred compounds of Formula (I) are those compounds according to Formula (I), the pharmaceutically acceptable acid or base addition salts thereof, the stereochemically isomeric forms thereof and the N-oxide form thereof, in which $R^3$ is hydrogen or alkyl, Z is N—$R^7$ wherein $R^7$ is hydrogen or alkyl, a is a single bond and b is a double bond, $R^4$ and $R^5$ together form a bivalent radical of Formula (c-1), (c-3), (c-5), (c-7), (c-8) or (c-10) wherein $R^7$ and $R^8$ are hydrogen and $R^9$ and $R^{10}$ together form a bivalent radical of formula —$CR^8$═$CR^8$—$CR^8$═$CR^8$— wherein $R^8$ is hydrogen.

More specifically, the compound 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido[1,2-α]benzimidazol-4(10H)-one, the pharmaceutically acceptable acid or base addition salts thereof, the stereochemically isomeric forms thereof and the N-oxide form thereof, are most preferred.

The pharmaceutically acceptable acid addition salts are defined to comprise the therapeutically active non-toxic acid addition salt forms which the compounds according to Formula (I) are able to form. Said acid addition salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (I) as well as the salts thereof, are able to form. Such solvates are, for example, hydrates and alcoholates.

Among the acid addition salts, the compound 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido[1,2-α]benzimidazol-4(10H)-one (E)-2-butenedioate (2:3) hydrate (1:1) including all stereoisomeric forms thereof is the most preferred compound.

Particularly preferred compounds are the (A)[(2α, 4β)(A)] enantiomer, the (B)[(2α,4β)(A)] enantiomer and a mixture thereof, of the compounds 3-[2-[4-(11,12-dihydro-6H-benzimidazo[2,1-b][3]benrazepin-6-yl)-2-(phenylmethyl)-1-piperidinyl]ethyl]-2,10-dimethylpyrimido[1,2-a]benzimidazol-4(10H)-one and 3-[2-[4-(11,12-dihydro-6H-benzimidazo[2,1-b][3]benzazepin-6-yl)-2-(phenylmethyl)-1-piperidinyl]

ethyl]-2,10-dimethyl pyrimido[1,2-a]benzimidazol-4(10H)-one (E)-2-butenedioate (2:3) hydrate (1:1).

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperidinyl radical in Formula (1) are N-oxidized.

The term "stereochemically isomeric forms" as used herein defines all possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R— or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When the bond at c is a single bond, compounds of Formula (I) and some of the intermediate compounds have at least two stereogenic centers in their structure. When $R^1$ is other than hydrogen, the monocyclic N-ring in Formula (I) has a further stereogenic center. This may lead to 8 stereochemically different structures.

The compounds of Formula (I) as prepared in the processes described below may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Some of the compounds of Formula (I) may also exist in their tautomeric form. Such forms although not explicitly indicated in the above formula are intended to be included within the scope of the present invention. For instance, compounds of Formula (I) wherein $R^5$ is H may exist in their corresponding tautomeric form.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp.112-176, and *Drugs,* 1985, 29, pp.455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a $C_{1-6}$alkyl, phenyl, benzyl or one of the following groups:

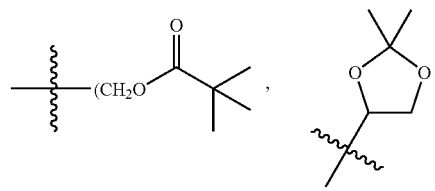

Amidated groups include groups of the formula —CONR$^y$R$^z$, wherein R$^y$ is H, $C_{1-6}$alkyl, phenyl or benzyl and R$^z$ is —OH, H, $C_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to Formula (1) can generally be prepared by a succession of steps, each of which is known to the skilled person. The preparation of said compounds is disclosed in a co-pending application, which is included herein by reference.

Apart form their use for reducing the ICP, the compounds according to Formula (I) and derivatives thereof are also useful for the treatment of other histamine H1- and H2-mediated diseases, in particular for immunomodulation in a mammal, for the suppression of hypersensitivity and/or inflammatory reactions, for the treatment and prevention of allergic diseases such as rhinitis, urticaria, asthma, anaphylaxis and the like and for the treatment of gastrointestinal conditions such as ulcers, dyspepsia, various reflux indications and the like. The invention is therefor also concerned with the use of an histamine receptor antagonist according to Formula (I) and derivatives thereof for the manufacture of a medicament for immunomodulation in a mammal, for the suppression of hypersensitivity and/or inflammatory reactions and for the treatment and prevention of allergic diseases and gastrointestinal conditions.

A further aspect of the invention is to provide for a new use for histamine H1- and/or H2-receptor antagonists, in particular for acutely lowering the intracranial pressure (ICP), in particular an elevated ICP, more in particular a critically elevated ICP and/or preventing an elevated ICP and secondary ischaemia caused by brain injury. Most advantageously, the histamine H1- and/or H2-receptor antagonists do not or to a minimum extend lower or raise the blood pressure.

According to the invention, the histamine H1- and/or H2-receptor antagonists are either compounds and derivatives thereof according to Formula (I) or known histamine H1- and/or H2-receptor antagonists, being a discrete and limited group of medications readily recognized in the art.

Hithertoo, histamine H1-receptor antagonists are commonly used for inmiunomodulation in a mammal and for the suppression of hypersensitivity and/or inflammatory reactions. In particular, the histamine H1-receptor antagonist is selected from the group of acrivastine, alimemazine, antazoline, astemizole, azatadine, azelastine, brompheniramine, buclizine, carbinoxamine, carebastine, cetirizine, chlorcyclizine, chlorpheniramine, cinnarizine, clemastine, clemizole, clocinizine, clonidine, cyclizine, cyproheptadine, descarboethoxyloratidine, dexchlorpheniramine, dimenhydrinate, dimethindene, dimethothiazine, diphenhydramine, diphenylpyraline, doxylamine, ebastine, efletirizine, epinastine, fexofenadine, hydroxyzine, ketotifen, levocabastine, loratidine, meclizine, mequitazine, methdilazine, mianserin, mizolastine, niaprazine, noberastine, norastemizole, oxatomide, oxomemazine, phenbenzamine, pheniramine, picumast, promethazine, pyrilamine, temelastine, terfenadine, trimeprazine, tripelennamine and triprolidine, derivatives thereof and mixtures of any two or more of the foregoing.

Hithertoo, histamine H2-receptor antagonists are commonly used for mamals suffering from certain gastrointestinal conditions such as ulcers, dyspepsia, various reflux indications and the like. In particular, the histamine H2-receptor antagonist is selected from the group of ranitidine, cimetidine, famotidine, nizatidine, tiotidine, zolantidine, derivatives thereof and mixtures of any two or more of the foregoing.

Also, histamine receptor antagonists may exhibit both histaminic H1- and/or H2-receptor antagonist activity, such as ritanserine or the compounds according to Formula (I), the pharmaceutically acceptable acid or base addition salts thereof, the stereochemically isomeric forms thereof and the N-oxide form thereof.

While all compounds show a marked depression of the ICP, the following compounds have been shown also to have no or little effect on the lowering of the blood pressure: ketotifen, chlorcyclizine, promethazine, pyrilamine, diphenylhydramine, chlorpheniramine and zolantadine.

In vitro studies can be used to evaluate the histamine antagonist activity of the present compounds using appropriate receptor modelling studies.

In vivo studies can be used to evaluate the biological activity of the present compounds. To this extent, a clinically relevant rat model for traumatic brain injury (Closed Head Injury-model) was developed and used to test the compounds according to the invention (K. Engelborghs et al., *Temporal changes in intracranial pressure in a modified experimental model of closed head injury*, J. Neurosurg. 89: 796-806, 1998; K. van Rossem et al., *Brain oxygenation after experimental closed head injury*, Adv. Exp. Med. Biol. 471: 209-215, 1999; K. Engelborghs et al., *Impaired autoregulation of cerebral bloodflow in an experimental model of traumatic brain injury*, J. Neurotrauma, 17(8): 667-677, 2000). In one study intracranial hypertension was induced by a cortical cold lesion in rabbits.

The histamine receptor antagonist according to the invention, including the compounds according to Formula (I) and the currently known histamine H1-, H2- and H1/H2-receptor antagonists may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Most preferably, —for ease of quick administration—the aforementioned pharmaceutical composition is formulated as an injectable or perfusable solution or suspension.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction.

For example, for the compound pyrimido[1,2-a]benzimidazol-4(10H)-one, 3-[2-[4-(11,12-dihydro-6H-benzimidazo[2,1-b][3]benzazepin-6-yl)-2-(phenylmethyl)-1-piperidinyl]ethyl]-2,10-dimethyl, the 8 possible stereochemical isomeric forms are defined as follows:

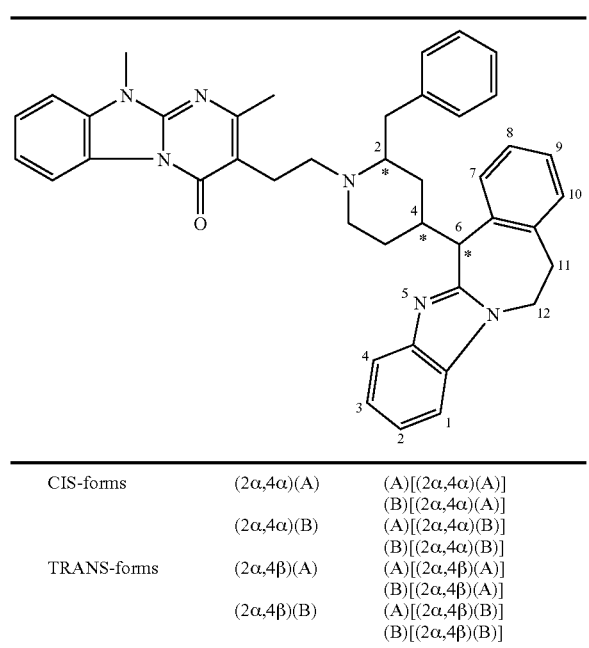

| CIS-forms | (2α,4α)(A) | (A)[(2α,4α)(A)] |
| | | (B)[(2α,4α)(A)] |
| | (2α,4α)(B) | (A)[(2α,4α)(B)] |
| | | (B)[(2α,4α)(B)] |
| TRANS-forms | (2α,4β)(A) | (A)[(2α,4β)(A)] |
| | | (B)[(2α,4β)(A)] |
| | (2α,4β)(B) | (A)[(2α,4β)(B)] |
| | | (B)[(2α,4β)(B)] |

Hereinabove and hereinafter, "DMF" is defined as N,N-dimethylformamide, "DIPE" is defined as diisopropyl ether, "THF" is defined as tetrahydrofurane, "MIBK" is defined as methyl isobutylketone, "DIPA" is defined as diisopropylamine.

A. Preparation of the Intermediate Compounds

EXAMPLE A1 a) Preparation of intermediate 1

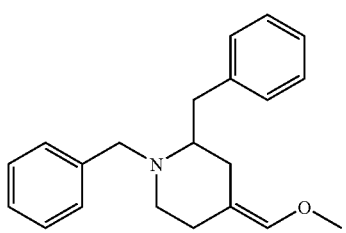

Use dry glassware. A mixture of (methoxymethyl)triphenylphosphoniumchloride (0.35 mol) in THF p.a.(mol. sieves) (2 l) was stirred at −50° C. under $N_2$ flow. BuLi, 2.5M/hexane (0.35 mol) was added dropwise and the mixture was stirred at −25° C. for 30 min. A solution of 1,2-bis(phenylmethyl)-4-piperidinone (0.35 mol) in THF was added dropwise at −25° C. The mixture was allowed to warm to room temperature, then stirred at room temperature overnight and decomposed with water. The organic solvent was evaporated. The aqueous concentrate was extracted with $CH_2Cl_2$. The organic layer was separated, dried ($MgSO_4$), filtered and the solvent was evaporated. The residue was purified by column chromatography over silica gel (eluent: $CH_2Cl_2/CH_3OH$ 97.5/2.5). The pure fractions were collected and the solvent was evaporated. Yielding: 121 g of 4-(methoxymethylene)-1,2-bis(phenylmethyl)piperidine enantiomeric mixture (intermediate 1) (100%).

b) Preparation of intermediate 2

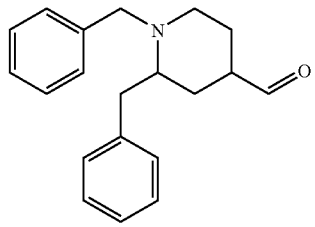

A mixture of intermediate 1 (0.35 mol) in THF (500 ml) was stirred till complete dissolution. $H_2O$ (900 ml) and then HCl p.a. 38% (100 ml) were added. The mixture was stirred and refluxed for 3 hours. The organic solvent was evaporated. The aqueous concentrate was alkalized with $K_2CO_3$ and extracted with $CH_2Cl_2$. The organic layer was separated, dried ($MgSO_4$), filtered and the solvent was evaporated. The residue was purified by column chromatography over silica gel (eluent: $CH_2Cl_2/CH_3OH$ 97/3). The pure fractions were collected and the solvent was evaporated. Yielding: 81 g of 1,2-bis(phenylmethyl)-4-piperidinecarboxaldehyde enantiomeric mixture (intermediate 2) (79%).

c) Preparation of intermediate 3

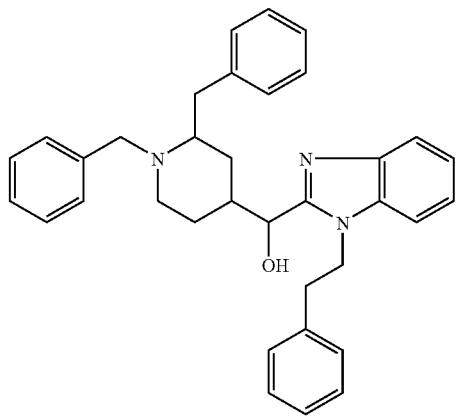

A mixture of DIPA (0.33 mol) in THF p.a. (previously dried on mol. sieves) (21) was stirred at −78° C. under $N_2$ flow. BuLi, 2.5M/hexane (0.276 mol) was added dropwise. The mixture was stirred at −78° C. for 15 min. A solution of 1-(2-phenylethyl)-1H-benzimidazole (0.276 mol) in THF was added dropwise. The mixture was stirred at −78° C. for 1 hour. A solution of intermediate 2 (0.276 mol) in THF was added dropwise. The mixture was stirred at −78° C. for 1 hour, then allowed to warm to room temperature, stirred at room temperature overnight and then decomposed with water. The organic solvent was evaporated. The aqueous concentrate was extracted with $CH_2Cl_2$. The organic layer was separated, dried ($MgSO_4$), filtered and the solvent was evaporated. The residue was purified by column chromatography over silica gel (eluent: CH$_2$Cl$_2$/CH$_3$OH 95/5 to 90/10). The pure fractions were collected and the solvent was evaporated. Yielding: 113 g of α-[1,2-bis(phenylmethyl)-4-piperidinyl]-1-(2-phenylethyl)-1H-benzimidazole-2-methanol (intermediate 3)(79%).

d) Preparation of intermediate 4

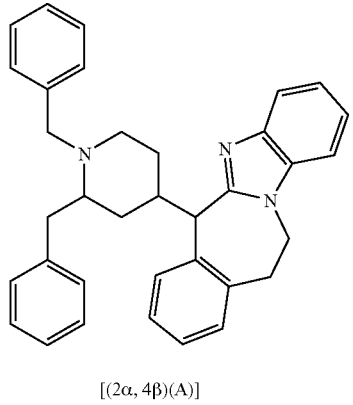

[(2α, 4β)(A)]

A mixture of intermediate 3 (0.22 mol) in trifluoromethanesulfonic acid (750 ml) was stirred at 110° C. for 7 hours. The mixture was cooled, poured out on ice, alkalized with NaOH 50% and extracted with CH$_2$Cl$_2$. The organic layer was separated, dried (MgSO$_4$), filtered and the solvent was evaporated. The residue was crystallized from CH$_3$CN. The mixture was filtered. The precipitate and the filtrate was purified separately by column chromatography over silica gel (eluent: CH$_2$Cl$_2$/CH$_3$OH 98.5/1.5 to 95/5). Four pure fractions were collected and their solvents were evaporated. The residues were crystallized from CH$_3$CN. The precipitates were filtered off and dried. Yielding: 16 g of fraction 1 [(2a, 4β)(A)]-6-[1,2-bis(phenylmethyl)-4-piperidinyl]-11,12-dihydro-6H-benzimidazo[2,1-b][3]benzazepine (intermediate 4) (14.6%), 19.5 g of fraction 2 [(2a,4β)(B)]-6-[1,2-bis(phenylmethyl)-4-piperidinyl]-11,12Aihydro-6H-benzimidazo[2,1-b][3]benzazepine (17.8%), 8.66 g fraction 3 [(2α,4α)(A)]-6-[1,2-bisphenylmethyl-4-piperidinyl]-11,12-dihydro-6H-benzimidazo[2,1-b][3]benzazepine (7.9%) and 7.74 g of fraction 4 [(2a,4α)(B)]-6-[1,2-bis(phenylmethyl)-4-piperidinyl]-11,12-dihydro-6H-benzimidazo[2,1-b][3]benzazepine (8.9%).

e) Preparation of intermediate 5

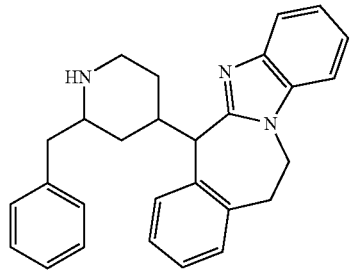

A mixture of intermediate 4 (0.0305 mol) in methanol (150 ml) was hydrogenated at 50° C. overnight with Pd/C 10% (1 g) as a catalyst. After uptake of H$_2$ (1 equiv), the catalyst was filtered off and the filtrate was evaporated. The residue was crystallized from CH$_3$CN. The precipitate was filtered off and dried. Yielding: 11.66 g of [(2a,4β)(A)]-11,12-dihydro-6-[2-(ghenylmethyl)4-piperidinyl]-6H-benzimidazo[2,1-b][3]benzazepine (intermediate 5) (94%).

EXAMPLE A2 a) Preparation of intermediate 6

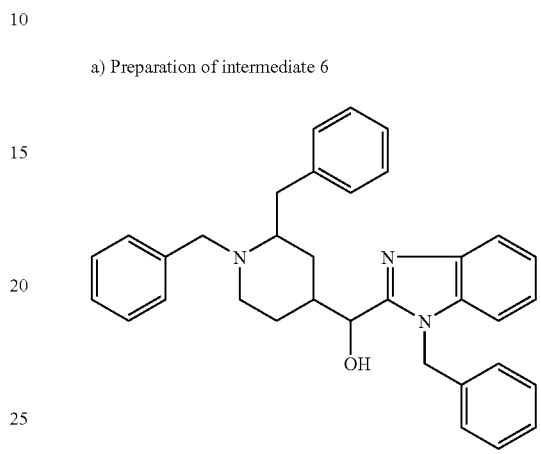

Use dry glassware. A mixture of DIPA (0.22 mol) in THF p.a.(previously dried on mol. sieves) (1400 ml) was stirred at –70° C. under N$_2$ flow. BuLi 2.5M (0.185 mol) was added dropwise and the mixture was stirred at –70° C. for 15 min. 1-(phenylmethyl)-1H-benzimidazole (0.185 mol) dissolved in THF was added dropwise at –70° C. and the mixture was stirred at –70° C. for 1 hour. Intermediate 2 (0.185 mol) dissolved in THF was added dropwise at –70° C. The mixture was stirred at –70° C. for 1 hour, then brought slowly to room temperature, stirred at room temperature overnight and decomposed with H$_2$O. The organic solvent was evaporated. The aqueous concentrate was extracted with CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH 95/5). The pure fractions were collected and the solvent was evaporated. Yielding: 91 g of intermediate 6 (98%).

b) Preparation of intermediate 7

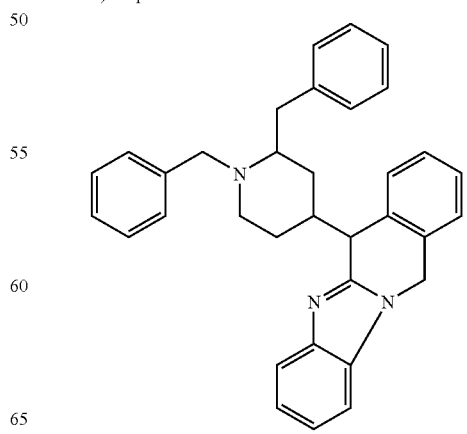

A mixture of intermediate 6 (0.18 mol) in trifluoromethanesulfonic acid (700 ml) was stirred at 120° C. under N₂ flow for 18 hours. The mixture was cooled, poured out on ice, alkalized with NaOH 50% and extracted with CH₂Cl₂. The organic layer was separated, dried (MgSO₄), filtered and the solvent was evaporated. The residue was purified by column chromatography over silica gel (eluent: CH₂Cl₂/ (CH₃OH/NH₃) 99/1). The pure fractions were collected and the solvent was evaporated. Yielding: 40 g of intermediate 7 (46%).

c) Preparation of intermediate 8

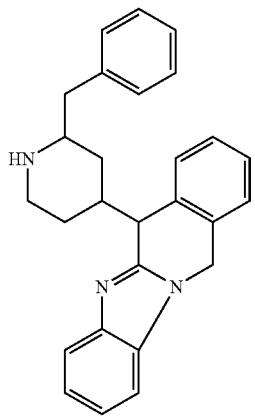

[(2α, 4β)(A)]

and preparation of intermediate 9

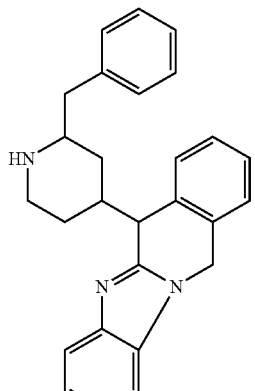

CIS

A mixture of intermediate 7 (0.081 mol) in methanol (200 ml) was hydrogenated at 50° C. with Pd/C 10% (2 g) as a catalyst. After uptake of H₂ (1 equiv), the catalyst was filtered off and the filtrate was evaporated. This fraction was purified by column chromatography over silica gel (eluent: CH₂Cl₂/ (CH₃OH/NH₃) 97/3). Two pure fractions were collected and their solvents were evaporated. Yielding: Fraction 1 and 12.5 g of intermediate 9 (cis isomers) (36%). Fraction 1 was crystallized from CH₃CN. The precipitate was filtered off and dried. Yielding: 4.44 g of intermediate 8 (14%) ([(2α,4β)(A)]-racemate.

EXAMPLE A3 a) Preparation of intermediate 10

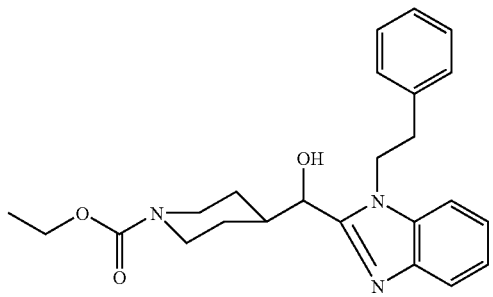

A mixture of DIPA (0.1 mol) in THF (100 ml) was stirred under N₂ flow. The mixture was cooled to −70° C. and BuLi, 2.5M/hexane (40 ml) was added portionwise. The temperature was allowed to reach −30° C., while stirring for 10 min. The mixture was cooled to −70° C. A solution of 1-(phenylethyl)-1H-benzimidazole (0.1 mol) in THF (50 ml) was added dropwise at this temperature and the mixture was stirred for 2 h at −70° C. Ethyl 4-formyl-1-piperidinecarboxylate (0.1 mol) was added dropwise and the mixture was stirred for 30 min at −70° C. The mixture was allowed to reach room temperature and stirring was continued for 30 min. The mixture was decomposed with water, then evaporated. The residue was stirred in water, and this mixture was extracted with CH₂Cl₂. The organic layer was separated, dried, filtered and the solvent was evaporated. The residue was purified by column chromatography over silica gel (eluent: CH₂Cl₂/CH₃OH 98/2). The pure fractions were collected and the solvent was evaporated. Yielding: 38 g of ethyl 4-[hydroxy[1-(2-phenylethyl)-1H-benzimidazol-2-yl]methyl]-1-piperidinecarboxylate (intermediate 10).

b) Preparation of intermediate 11

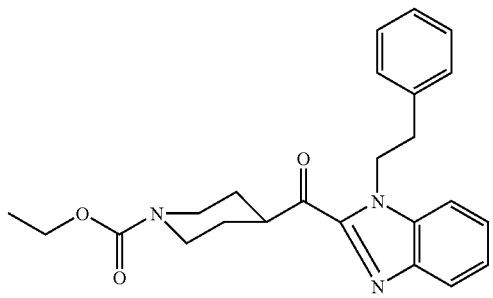

A mixture of intermediate 10 (0.011 mol) and MnO₂ (15 g) in CH₂Cl₂ (150 ml) was stirred overnight at room temperature. MnO₂ was filtered off over dicalite. The reaction was performed a second time with identical quantities. The mixture was stirred overnight. MnO₂ was filtered off over dicalite. The filtrate was evaporated. Yielding: 4.5 g ethyl 4-[[1-(2-phenylethyl)-1H-benzimidazol-2-yl]carbonyl]-1-piperidinecarboxylate (intermediate 11).

c) Preparation of intermediate 12

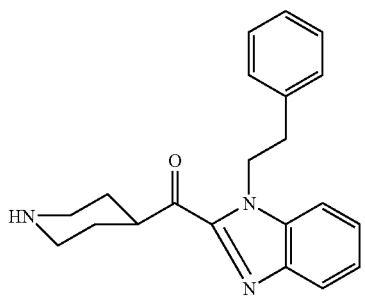

A mixture of intermediate 11 (0.011 mol) and HBr, 48% aq. (25 ml) was stirred for 10 h at 80° C. The solvent was evaporated. The residue was stirred in boiling 2-propanol, cooled and the resulting precipitate was filtered off and dried. A sample (1 g) was recrystallized from ethanol. The crystals were filtered off and dried. Yielding: 0.5 g of [1-(2-phenylethyl)-1H-benzimidazol-2-yl](4-piperidinyl)methanone dihydrobromide (intermediate 12) (mp. 261.9° C.).

d) Preparation of intermediate 13

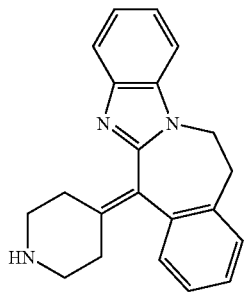

Trifluoromethanesulfonic acid (150 ml) was stirred under $N_2$ flow. Intermediate 12 (0.1 mol) was added portionwise and the resulting reaction mixture was stirred for 20 h at 100° C. ($N_2$ flow). The reaction mixture was cooled, poured out into ice (1 kg) and the resulting mixture was neutralized with NaOH 50%, while stirring and cooling. This mixture was extracted with $CH_2Cl_2$. Precipitation resulted. The organic layer was separated. The precipitate was filtered off and recrystallized from $CH_3CN$. The crystals were filtered off and recrystallized again from $CH_3CN$. The crystals were filtered off and dried. Yielding: 3.0 g of 11,12-dihydro-6-(4-piperidinylidene)-6H-benzimidazo[2,1-b][3]benzazepine.trifluoromethanesulfonate (2:3). The separated organic liquor was combined with the mother layers, dried, filtered and the solvent was evaporated. The residue (37 g) was dissolved in water/ethanol, alkalized with 50% NaOH and extracted with $CH_2Cl_2$. The separated organic layer was dried ($MgSO_4$), filtered and the solvent was evaporated. The residue was stirred in 2-propanone/DIPE, then filtered off and dried. Yielding: 16.2 g of 11,12-dihydro-6-(4-piperidinylidene)-6H-benzimidazo[2,1-b][3]benzazepine (intermediate 13) (mp. 180.3° C.).

EXAMPLE A4 a) Preparation of intermediate 14

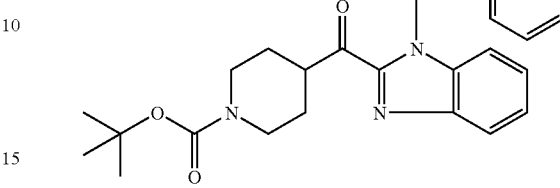

Use dry glassware. A mixture of DIPA (1.1 mol) in THF p.a. (previously dried on mol. sieves) (3000 ml) was stirred at −78° C. under $N_2$ flow. BuLi 1.5M in hexane (1.05 mol) was added dropwise at −70° C. and the mixture was stirred at −70° C. for 20 min. 1-(phenylethyl)-1H-benzimidazole (1 mol) dissolved in THF was added dropwise at −78° C. and the mixture was stirred at −78° C. for 1 hour. 4-ethyl 1-(1,1-dimethyl)1,4-piperidinedicarboxylate (1.1 mol) dissolved in THF was added dropwise at −70° C. The mixture was stirred at −78° C. for 1 hour, then brought to room temperature, stirred at room temperature overnight and decomposed with $H_2O$. The organic solvent was evaporated. The aqueous concentrate was extracted with $CH_2Cl_2$. The organic layer was separated, dried ($MgSO_4$), filtered and the solvent was evaporated. The residue was crystallized from $CH_3CN$. The precipitate was filtered off and dried. Yielding: 350 g of intermediate 14 (81%).

b) Preparation of intermediate 15

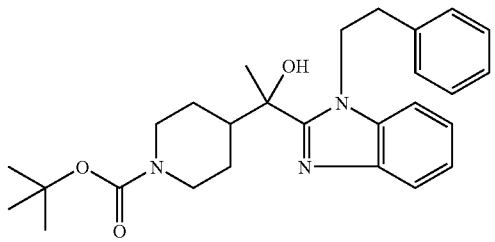

Reaction under $N_2$ atmosphere. Methylmagnesium chloride (0.0165 mol; 8.2 ml, 2.0 M/THF) was added dropwise to a solution of intermediate 14 (0.0150 mol) in THF (90 ml), stirred at room temperature. The resulting reaction mixture was stirred for 2 hours. Water was added. The organic solvent was evaporated and the aqueous concentrate was extracted with $CH_2Cl_2$. The separated organic layer was dried, filtered and the solvent evaporated. The residue (6 g) was crystallized from $CH_3CN$. The precipitate was filtered off and dried. Yielding: 4.3 g of intermediate 15 (64%).

c) Preparation of intermediate 16

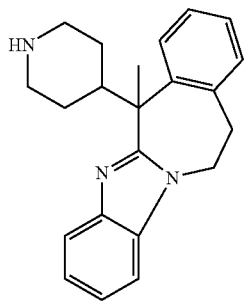

A mixture of intermediate 15 (0.0076 mol) in trifluoromethanesulfonic acid (29 ml) was stirred for 48 hours at room temperature. The reaction mixture was poured out into water. This mixture was alkalized with $K_2CO_3$. The aqueous layer was extracted with $CH_2Cl_2$. The separated organic layer was dried, filtered and the solvent evaporated. The residue was purified by short open column chromatography over silica gel (eluent: $CH_2Cl_2/(CH_3OH/NH_3)$ 90/10). The pure fractions were collected and the solvent was evaporated. Yielding: 2 g of intermediate 16 (79%).

EXAMPLE A5 a) Preparation of intermediate 17

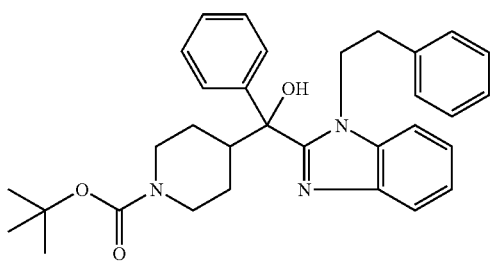

Reaction under $N_2$ atmosphere. Phenylmagnesium chloride (0.0440 mol) was added to a solution of intermediate 14 (0.0400 mol) in THF (200 ml), stirred at room temperature. The resulting reaction mixture was stirred for one hour. Water was added. The organic solvent was evaporated and the aqueous concentrate was extracted with is $CH_2Cl_2$. The separated organic layer was dried, filtered and the solvent evaporated. This residue was combined with analogously obtained material and the whole (20 g) was crystallized from $CH_3CN$. The precipitate was filtered off and dried. Yielding: 20 g of intermediate 17 (98%).

b) Preparation of intermediate 18

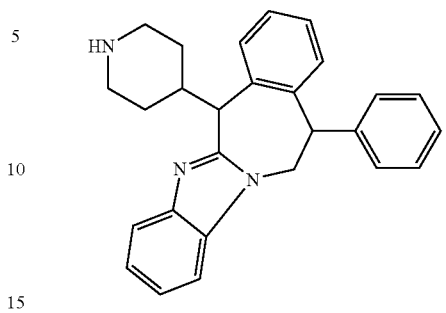

A mixture of intermediate 17 (0.0360 mol) in trifluoromethanesulfonic acid (120 ml) was stirred for 24 hours, going from 0° C. to room temperature. The reaction mixture was poured out into water. This mixture was alkalized with NaOH 50%, then extracted with $CH_2Cl_2$. The separated organic layer was dried, filtered and the solvent evaporated. The residue was crystallized from $CH_3CN$, filtered off, then purified by short open column chromatography over silica gel (eluent: $CH_2Cl_2/(CH_3OH/NH_3)$ 90/10). The pure fractions were collected and the solvent was evaporated. Yielding: 11 g of intermediate 18 (78%).(mp. 270.7° C.)

EXAMPLE A6 a) Preparation of intermediate 19

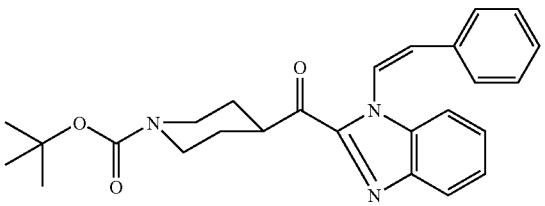

A mixture of 1-(2-phenylethenyl)-1H-benzimidazole (0.04 mol) in THF (100 ml) was stirred under $N_2$ flow and cooled to −70° C. BuLi, 2.5 M/hexane (0.04 mol) was added dropwise at −70° C. and stiring was continued for 30 min at −70° C. A solution of 4-ethyl 1-(1,1-dimethylethyl)-1,4-piperidinedicarboxylate (0.04 mol) in THF was added dropwise and the mixture was stirred for 1 h at −70° C. The temperature was allowed to reach room temperature and the mixture was decomposed with water, then extracted with $CH_2Cl_2$. The separated organic layer was dried ($MgSO_4$), filtered and the solvent was evaporated. The residue was purified by column chromatography over silica gel (eluent: $CH_2Cl_2/CH_3CN$ 97/3 upgrading to 94/6). Two fractions were collected and the solvent was evaporated. The second fraction's residue was crystallized from $DIPE/CH_3CN$. The crystals were filtered off and dried. Yielding: 7.0 g of (1,1-dimethylethyl) (Z)-4-[[1-(2-phenylethenyl)-1H-benzimidazol-2-yl]carbonyl]-1-piperidinecarboxylate (41%) (intermediate 19). (mp. 155.8° C.)

b) Preparation of intermediate 20

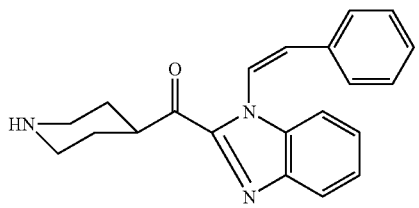

A mixture of intermediate 19 (0.043 mol) in trifluoroacetic acid (130 ml) was stirred for ½ hour at room temperature. The reaction mixture was poured out into diethylether. The precipitate was filtered off, washed with diethylether and dried. Yielding: 18 g of (Z)-[1-(2-phenylethenyl)-1H-benzimidazol-2-yl](4-piperidinyl)methanone trifluoroacetate (1:1) (intermediate 20) (94.0%). (mp. 202.2° C.)

c) Preparation of intermediate 21

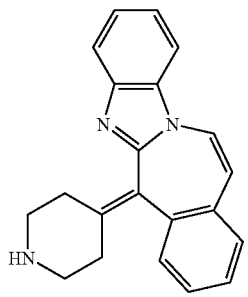

A mixture of intermediate 20 (0.0276 mol), $AlCl_3$ (0.187 mol) and NaCl (0.187 mol) was stirred for 1 hour at 150° C. (melt). The reaction mixture was decomposed in a mixture of ice, water and NaOH 50%. The mixture was extracted with dichloromethane and the organic layer was separated, dried, filtered and evaporated. The residue (4.3 g) was purified on a glass filter over silica gel (eluent: $CH_2Cl_2/(CH_3OH/NH_3)$ 90/10). The pure fractions were collected and the solvent was evaporated. The residue was converted into the (E)-2-butenedioic acid salt (2:3) in ethanol. The salt was filtered off and dried. Yielding: 1.8 g of 6-(4-piperidinylidene)-6H-benzimidazo[2,1-b][3]benzazepine.(E)-2-butenedioate (2:3) (13.4%) (intermediate 21). (mp. 229.4° C.)

EXAMPLE A7 a) Preparation of intermediate 22

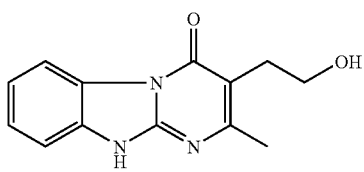

A mixture of 2-amine-1H-benzimidazole (0.04 mol), 3-acetyldihydro-2(3H)-furanone (0.53 mol) and 4-methylbenzenesulfonic acid (4 g) in xylene (930 ml) was stirred and refluxed overnight and then cooled. The precipitate was filtered off and stirred in $H_2O$ (200 ml), $Na_2CO_3$ (5 g) and $CH_2Cl_2$ (500 ml). The precipitate was filtered off, boiled in $CH_3OH$, filtered off and dried. Yielding: 47.4 g of 3-(2-hydroxyethyl)-2-methyl-pyrimido[1,2-a]benzimidazol-4(10H)-one (intermediate 22).

b) Preparation of intermediate 23

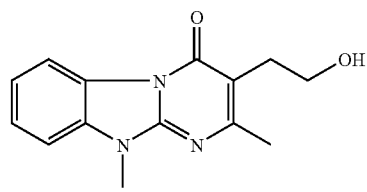

A mixture of intermediate 22 (0.025 mol) and $K_2CO_3$ p.a. (0.03 mol) in DMF (70 ml) was stirred at 50° C. Methyliodide (0.03 mol) was added dropwise. The mixture was stirred at 50° C. for 4 hours and cooled. The solvent was evaporated. The residue was boiled in $CH_3OH$. The precipitate was filtered off and dried. The residue was purified by HPLC over silica gel (eluent: $CH_2Cl_2/(CH_3OH/NH_3)$ 97/3). Two pure fractions were collected and their solvents were evaporated. Yielding: 2.08 g of 3-(2-hydroxyethyl)-2,10-dimethyl-pyrimido[1,2-a]benzimidazol-4(10H)-one (intermediate 23).

c) Preparation of intermediate 24

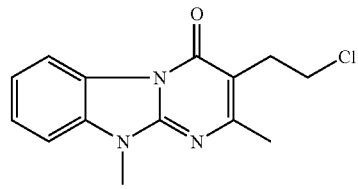

A mixture of intermediate 23 (0.02 mol) and $SOCl_2$ (0.06 mol) in $CHCl_3$ (50 ml) was stirred and refluxed for 4 hours and then cooled. $H_2O$ was added. The mixture was alkalized with $K_2CO_3$ and separated into its layers. The aqueous layer was extracted with $CH_2Cl_2$. The combined organic layer was dried ($MgSO_4$), filtered and the solvent was evaporated. The residue was crystallized from $CH_3CN$. The precipitate was filtered off and dried. Yielding: 3.44 g of intermediate 24.

B. Preparation of the Final Compounds
EXAMPLE B1
Preparation of compound 1
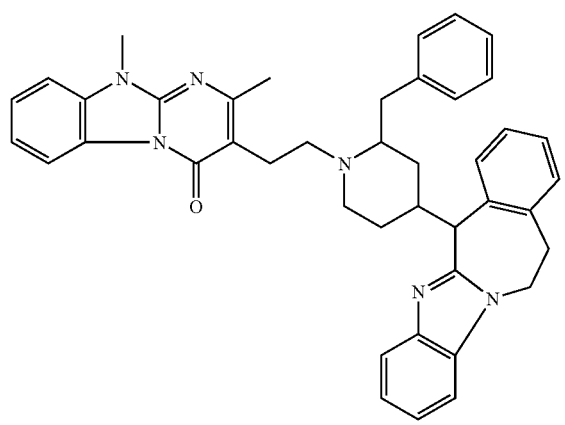
B-[(2α, 4β)(A)]
and preparation of compound 2
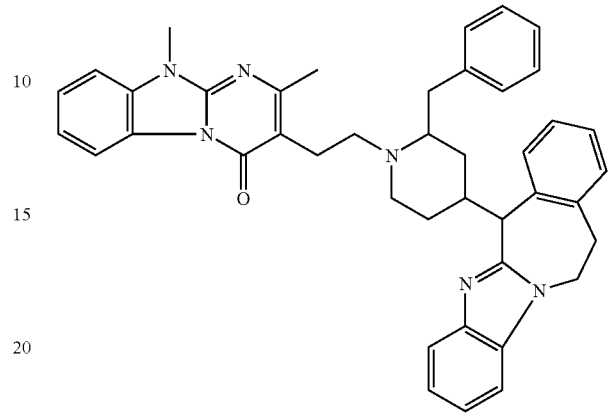
A-[(2α, 4β)(A)]
TABLE 1
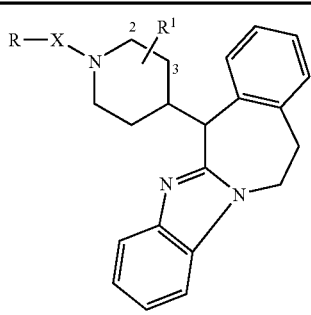
| Co. nr. | Ex. nr. | R¹ | R | X | Phys. data and stereochemistry |
|---|---|---|---|---|---|
| 9 | B1 | 2-benzyl | 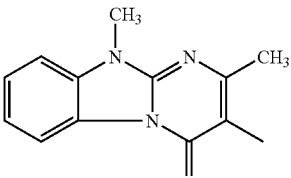 | —CH₂—CH₂— | [(2a,4a)(B)] |
| 10 | B1 | 2-benzyl | 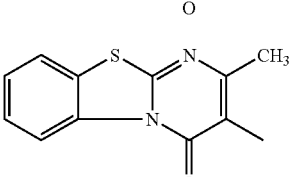 | —CH₂—CH₂— | [(2a,4a)(B)] |
| 11 | B1 | 2-benzyl | 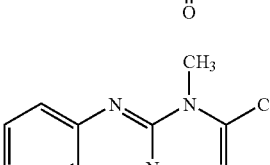 | —CH₂—CH₂— | [(2a,4a)(B)]; .H₂O(1:2) |

TABLE 1-continued

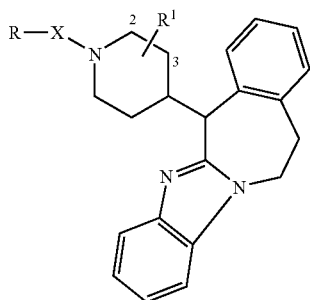

| Co. nr. | Ex. nr. | R¹ | R | X | Phys. data and stereochemistry |
|---|---|---|---|---|---|
| 12 | B1 | 2-benzyl | 10-ethyl-2,3-dimethyl-pyrimido[1,2-a]benzimidazol-4(10H)-one | —CH₂—CH₂— | [(2a,4a)(B)] |
| 13 | B1 | 2-benzyl | 2,3,10-trimethyl-pyrimido[1,2-a]benzimidazol-4(10H)-one | —CH₂—CH₂— | [(2a,4μ)(B)] |
| 14 | B1 | H | 2,3,10-trimethyl-pyrimido[1,2-a]benzimidazol-4(10H)-one | —CH₂—CH₂— | |
| 15 | B1 | 2-benzyl | 2,3,10-trimethyl-pyrimido[1,2-a]benzimidazol-4(10H)-one | —CH₂—CH₂— | [(2a,4β)(A)]; (E)-2-butenedioate(2:3) |
| 16 | B1 | 2-benzyl | 2,3,10-trimethyl-pyrimido[1,2-a]benzimidazol-4(10H)-one | —CH₂—CH₂— | [A(2a,4α)(B)] |

TABLE 1-continued

| Co. nr. | Ex. nr. | R¹ | R | X | Phys. data and stereochemistry |
|---|---|---|---|---|---|
| 17 | B1 | 2-benzyl | | —CH$_2$—CH$_2$— | [B(2a,4α)(B)] |
| 18 | B1 | 2-methyl cyclohexy | | —CH$_2$—CH$_2$— | |
| 19 | B1 | 2-benzyl | | —CH$_2$—CH$_2$— | [(2a,4α)(B)] |
| 20 | B1 | 2-benzyl | | —CH$_2$—CH$_2$— | [(2a,4α)(B)] |
| 21 | B1 | 2-benzyl | | —CH$_2$—CH$_2$— | [(2a,4α)(B)] |

TABLE 1-continued
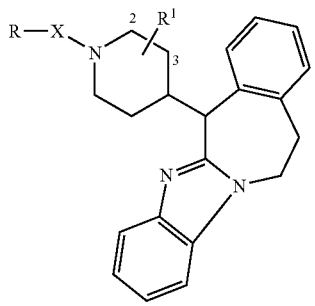
| Co. nr. | Ex. nr. | R¹ | R | X | Phys. data and stereochemistry |
|---|---|---|---|---|---|
| 22 | B1 | 2-benzyl | 4-fluorobenzyl-2,3-dimethyl-pyrimido[1,2-a]benzimidazol-4(1H)-one | —CH₂—CH₂— | [(2a,4α)(B)] |
| 23 | B1 | 2-benzyl | 1-(2-ethoxyethyl)-2,3-dimethyl-pyrimido[1,2-a]benzimidazol-4(1H)-one | —CH₂—CH₂— | [(2a,4α)(B)] |
| 24 | B1 | 2-benzyl | 1-(3,5-dimethylbenzyl)-2,3-dimethyl-pyrimido[1,2-a]benzimidazol-4(1H)-one | —CH₂—CH₂— | [(2a,4α)(B)] |
| 25 | B1 | 2-benzyl | 1,2,3,7,8-pentamethyl-pyrimido[1,2-a]benzimidazol-4(1H)-one | —CH₂—CH₂— | [(2a,4α)(B)] |

TABLE 1-continued

| Co. nr. | Ex. nr. | R¹ | R | X | Phys. data and stereochemistry |
|---|---|---|---|---|---|
| 26 | B1 | 2-benzyl | (3,5-dimethylbenzyl attached to 2,3-dimethyl-4-oxo-pyrimido-benzimidazole) | —CH₂—CH₂— | [(2a,4α)(B)]; .H₂O(1:1) |
| 27 | B1 | 2-benzyl | ((6-methylpyrazin-2-yl)methyl attached to 2,3-dimethyl-4-oxo-pyrimido-benzimidazole) | —CH₂—CH₂— | [(2a,4α)(B)] |
| 28 | B1 | 2-benzyl | ((5-methylpyrazin-2-yl)methyl attached to 2,3-dimethyl-4-oxo-pyrimido-benzimidazole) | —CH₂—CH₂— | [(2a,4α)(B)] |
| 29 | B1 | 2-benzyl | (2-methoxyethoxymethyl attached to 2,3-dimethyl-4-oxo-pyrimido-benzimidazole) | —CH₂—CH₂— | [(2a,4α)(B)] |

TABLE 1-continued
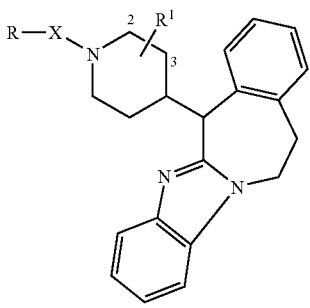
| Co. nr. | Ex. nr. | R¹ | R | X | Phys. data and stereochemistry |
|---|---|---|---|---|---|
| 30 | B1 | 2-benzyl | 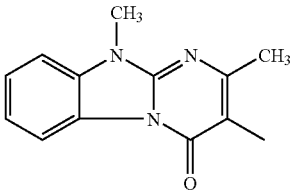 | —CH₂—CH₂— | [(2a,4α)(A)] |
| 31 | B1 | 2-benzyl | 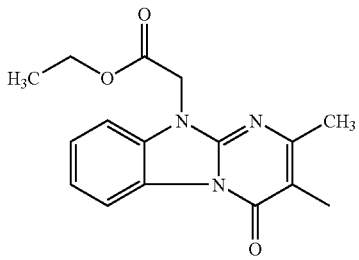 | —CH₂—CH₂— | [(2a,4α)(B)] |
| 32 | B1 | 2-benzyl | 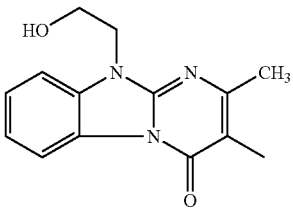 | —CH₂—CH₂— | [(2a,4α)(B)] |
| 33 | B1 | 2-benzyl |  | —CH₂—CH₂— | [(2a,4α)(B)] |

TABLE 1-continued

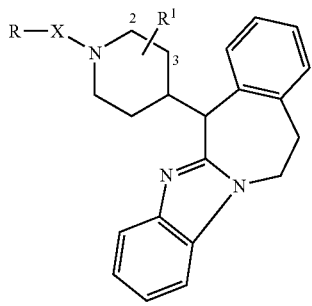

| Co. nr. | Ex. nr. | R¹ | R | X | Phys. data and stereochemistry |
|---|---|---|---|---|---|
| 34 | B1 | 2-benzyl | phthalimide-N-CH₂CH₂- linked to benzimidazo-pyrimidinone (2,3-dimethyl) | —CH₂—CH₂— | [(2a,4α)(B)]; .H₂O(1:1) |
| 35 | B1 | 2-benzyl | CH₃O-CH₂CH₂-O-CH₂CH₂- linked to benzimidazo-pyrimidinone (2,3-dimethyl) | —CH₂—CH₂— | [(2a,4α)(B)]; .H₂O(1:1) |
| 36 | B1 | 2-benzyl | H₂N-C(=O)-CH₂- linked to benzimidazo-pyrimidinone (2,3-dimethyl) | —CH₂—CH₂— | [(2a,4α)(B)]; .H₂O(1:1) |
| 37 | B1 | 2-benzyl | HO-CH₂CH₂-O-CH₂CH₂- linked to benzimidazo-pyrimidinone (2,3-dimethyl) | —CH₂—CH₂— | [(2a,4α)(B)] |

TABLE 1-continued

| Co. nr. | Ex. nr. | R¹ | R | X | Phys. data and stereochemistry |
|---|---|---|---|---|---|
| 38 | B1 | 2-benzyl | H₃C–C(=O)–O–CH₂–CH₂–O–CH₂–CH₂– attached to N of pyrimido-benzimidazolone (2,3-dimethyl-4-oxo) | —CH₂—CH₂— | [(2a,4α)(B)]; .H₂O(1:1) |
| 39 | B1 | 2-benzyl | HO–CH₂–CH(OH)–CH₂– attached to N of 2,3-dimethyl-4-oxo-pyrimido-benzimidazole | —CH₂—CH₂— | [(2a,4α)(B)]; .H₂O(1:1) |
| 40 | B1 | 2-benzyl | H₂N–CH₂–CH₂– attached to N of 2,3-dimethyl-4-oxo-pyrimido-benzimidazole | —CH₂—CH₂— | [(2a,4α)(B)] |
| 41 | B1 | 2-benzyl | CH₃–C(=O)–NH–CH₂–CH₂– attached to N of 2,3-dimethyl-4-oxo-pyrimido-benzimidazole | —CH₂—CH₂— | [(2a,4α)(B)] |

TABLE 1-continued
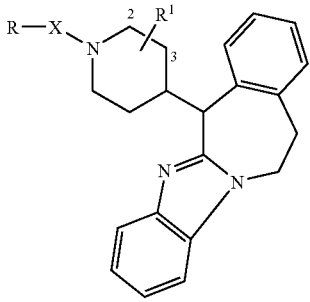
| Co. nr. | Ex. nr. | R[1] | R | X | Phys. data and stereochemistry |
|---|---|---|---|---|---|
| 42 | B1 | 2-benzyl | 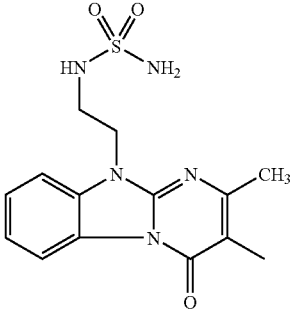 | —CH$_2$—CH$_2$— | [(2a,4α)(B)] |
| 43 | B1 | 2-benzyl | 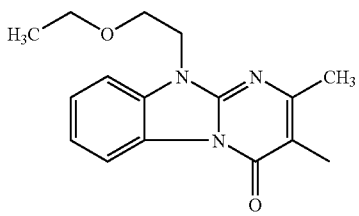 | (CH$_2$)$_2$—C(=O) | [(2a,4α)(A)] |
| 44 | B1 | 2-benzyl | 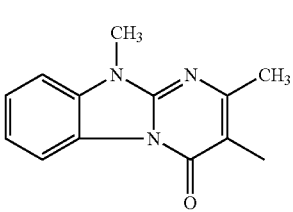 | —CH$_2$—CH$_2$— | [A(2a,4α)(A)] |
| 45 | B1 | 2-benzyl | 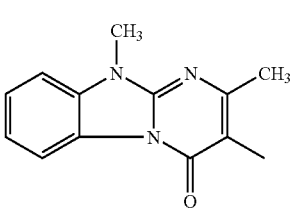 | —CH$_2$—CH$_2$— | [B(2a,4β)(A)] |
| 46 | B1 | 2-benzyl | 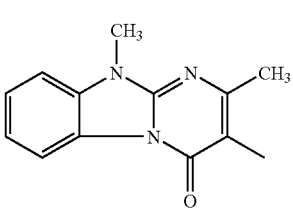 | —CH$_2$—CH$_2$— | [A(2a,4β)(B)]; Tri-fluoroacetate(1:1) |

TABLE 1-continued
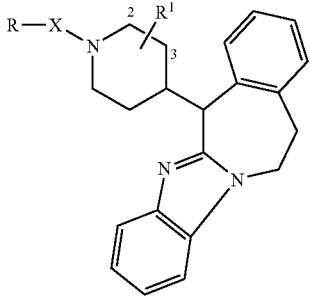
| Co. nr. | Ex. nr. | R¹ | R | X | Phys. data and stereochemistry |
|---|---|---|---|---|---|
| 47 | B1 | 2-benzyl | 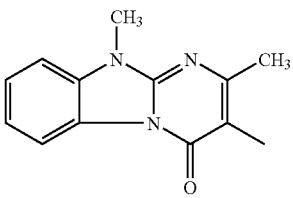 | —CH₂—CH₂— | [B(2a,4β)(B)]; Tri-fluoroacetate(1:1) |
| 48 | B1 | 2-benzyl | 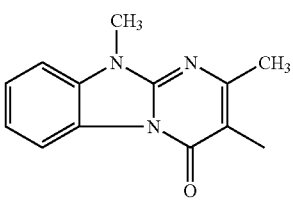 | —CH₂—CH₂— | [(2a,4β)(A)] |
| 49 | B1 | 2-benzyl | 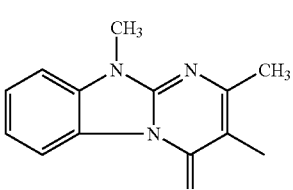 | —CH₂—CH₂— | [(2a,4β)(A)]; (−)-[S(R*,R*)]-2,3-dihydroxy butanedioate(1:2) |
| 50 | B1 | 2-benzyl | 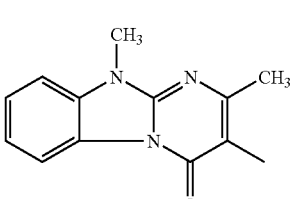 | —CH₂—CH₂— | [(2a,4β)(A)]; .HCl(1:3).H2O (1:2) |
| 51 | B1 | 2-benzyl | 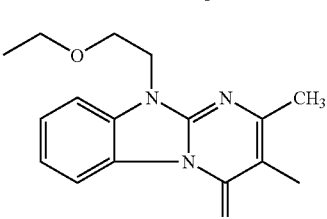 | CH₂—CH₂—CH | [(2a,4β)(A)]; .H2O(1:2) |
| 52 | B1 | 2-benzyl | 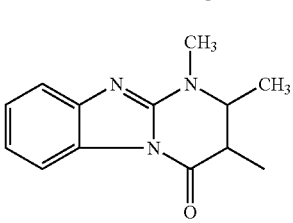 | —CH₂—CH₂— | [(2a,4β)(A)] |

TABLE 1-continued

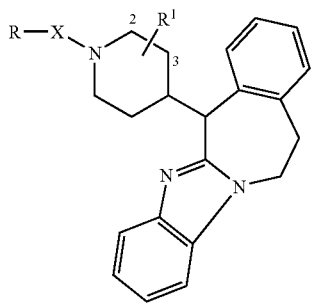

| Co. nr. | Ex. nr. | R¹ | R | X | Phys. data and stereochemistry |
|---|---|---|---|---|---|
| 53 | B1 | 2-benzyl | ethyl ester-substituted pyrimido-benzimidazolone | —CH$_2$—CH$_2$— | [(2α,4β)(A)] |
| 54 | B1 | 2-benzyl | ethyl ester-substituted pyrimido-benzimidazolone | —CH$_2$—CH$_2$— | [(2α,4β)(A)]; (E)-2-butenedioate(1:1) |
| 55 | B1 | 2-benzyl | methyl-substituted pyrimido-benzimidazolone | —CH$_2$—CH$_2$— | [(2α,4β)(A)]; (E)-2-butenedioate (1:1).H$_2$O(1:2) |
| 2 | B1 | 2-benzyl | methyl-substituted pyrimido-benzimidazolone | —CH$_2$—CH$_2$— | [A(2α,4β)(A)]; (E)-2-butenedioate (2:3).H$_2$O(1:1) |
| 1 | B1 | 2-benzyl | methyl-substituted pyrimido-benzimidazolone | —CH$_2$—CH$_2$— | [B(2α,4β)(A)]; (E)-2-butenedioate (2:3).H$_2$O(1:1) |

TABLE 1-continued

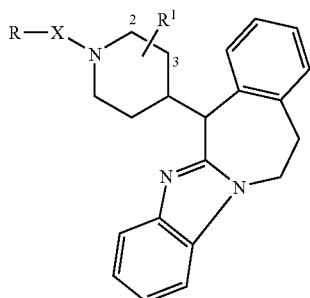

| Co. nr. | Ex. nr. | R¹ | R | X | Phys. data and stereochemistry |
|---|---|---|---|---|---|
| 56 | B1 | 2-benzyl | thiazolo[3,2-a]pyrimidinone with CH₃, CH₃ | CH₂—CH₂—CH | [(2a,4α)(B)] |
| 57 | B1 | 2-benzyl | N-methyl benzimidazo-pyrimidinone with CH₃, CH₃ | —CH₂—CH₂— | [A(2a,4α)(A)] |
| 58 | B1 | 2-benzyl | N-methyl benzimidazo-pyrimidinone with CH₃, CH₃ | —CH₂—CH₂— | [B(2a,4α)(A)] |
| 59 | B1 | 2-benzyl | thiazolo[3,2-a]pyrimidinone with CH₃, CH₃ | (CH₂)₂—N(C(O)CH₂CH₃)—(CH₂)₂— | [(2a,4α)(A)] |
| 60 | B1 | 2-benzyl | pyrido-pyrimidinone with CH₃, N-CH₃ | —CH₂—CH₂— | [(2a,4α)(B)] |

TABLE 1-continued

| Co. nr. | Ex. nr. | R¹ | R | X | Phys. data and stereochemistry |
|---|---|---|---|---|---|
| 109 | B1 | 2-benzyl | (thiazolo-pyrimidinone with CH₃, CH₃) | —CH₂— | [(2α,4α)(B)] |
| 152 | B1 | H | (benzothiazolo-pyrimidinone with CH₃, CH₃) | —CH₂—CH₂— | |
| 153 | B1 | H | (pyrido-pyrimidinone with CH₃, CH₃) | CH₂—CH₂—CH | (E)-2-Butenedioate (2:5) |

TABLE 2

| Comp. nr | Ex. nr. | R¹ | R⁵ ⌒ R⁴ | Phys. data and stereochemistry |
|---|---|---|---|---|
| 61 | B2 | H | —CH=CH—S— | |
| 62 | B2 | H | —CH₂—CH₂—S— | |
| 63 | B2 | H | —CH₂—CH₂—CH₂—S— | |
| 64 | B2 | H | —CH=CH—CH=CH— | |
| 65 | B2 | H | —CH₂—C(CH₃)=N—N(CH₃)— | |
| 66 | B2 | H | —C(CH₃)=N—N(CH₃)— | |
| 67 | B2 | H | —CH=CH—N(CH₃)— | |
| 68 | B2 | H | —O—C(CH₃)=CH— | |

TABLE 2-continued

| Comp. nr | Ex. nr. | R¹ | R⁵ R⁴ | Phys. data and stereochemistry |
|---|---|---|---|---|
| 69 | B2 | H | —CH=C(CH₃)—N(CH₃)— | |
| 70 | B2 | H | —CH=C(CH₃)—CHCH— | |
| 71 | B2 | H | —C(CH₃)=CH—S— | |
| 72 | B2 | H | —CH=CH—C(CH₃)— | |
| 73 | B2 | 2-benzyl | —CH=CH—S— | [(2α,4β)(B)] |
| 74 | B2 | 2-benzyl | —CH=CH—S— | [(2α,4α)(A)] |
| 75 | B2 | 2-benzyl | —CH=CH—S— | [(2α,4α)(B)] |
| 76 | B2 | 2-benzyl | —CH=CH—S— | [(2α,4β)(A)]; (E)-2-butenedioate (1:2)ethanolate(1:1) |
| 77 | B2 | 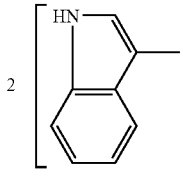 | —CH=CH—S— | [(2α,4α)(A)] |
| 78 | B2 | 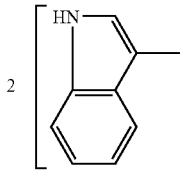 | —CH=CH—S— | [(2α,4β)(B)] |
| 79 | B2 | 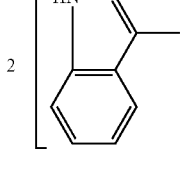 | —CH=CH—S— | [(2α,4α)(B)] |
| 80 | B2 | 2-benzyl | —CH=CH—CH=CH— | [(2α,4α)(B)] |
| 81 | B2 | 2-benzyl | —CH=CH—CH=CH— | [(2α,4β)(A)] |
| 82 | B2 | 2-benzyl | —CH=CH—CH=CH— | [(2α,4β)(B)] |
| 83 | B2 | 2-methylnaphthyl | —CH=CH—S— | [(2α,4β)(A)] |
| 84 | B2 | 2-methylnaphthyl | —CH=CH—S— | [(2α,4β)(B)] |
| 85 | B2 | 2-methylnaphthyl | —CH=CH—S— | [(2α,4α)(B)] |
| 86 | B2 | 2-methylnaphthyl | —CH=CH—S— | [(2α,4α)(A)]; .H₂O (1:1)ethanolate(1:1) |
| 87 | B2 | 3-methyl | —CH=CH—S— | A-trans |
| 88 | B2 | 3-methyl | —CH=CH—S— | B-trans |
| 89 | B2 | 3-methyl | —CH=CH—CH=CH— | [(3α,4β)(B)] |
| 90 | B2 | 3-methyl-(4-fluorophenyl) | —CH=CH—S— | [(2α,4β)(A)] |

TABLE 2-continued

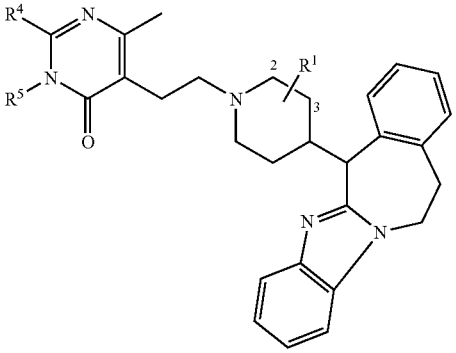

| Comp. nr | Ex. nr. | R¹ | R⁵ R⁴ | Phys. data and stereochemistry |
|---|---|---|---|---|
| 91 | B2 | 3-methyl-(4-fluorophenyl) | —CH=CH—S— | [(2α,4β)(B)] |
| 92 | B2 | 3-methyl-(4-fluorophenyl) | —CH=CH—S— | [(2α,4α)(A)] |
| 93 | B2 | 3-methyl-(4-fluorophenyl) | —CH=CH—S— | [(2α,4α)(B)] |
| 94 | B2 | 3-methyl | —CH=CH—CH=CH— | [(3α,4β)(A)] |
| 95 | B2 | 2-benzyl | —CH=C(CH$_3$)—N(CH$_3$)— | [(2α,4α)(B)] |
| 96 | B2 | 2-benzyl | —CH=CH—N(CH$_3$)— | [(2α,4α)(B)] |
| 97 | B2 | 2-benzyl | —CH=CH—C(CH$_3$)— | [(2α,4α)(B)] |
| 98 | B2 | 2-benzyl | —CH$_2$—CH$_2$—S— | [(2α,4α)(B)] |
| 99 | B2 | 2-benzyl | —CH$_2$—C(CH$_3$)=N—N(CH$_3$)— | [(2α,4α)(B)] |
| 100 | B2 | 2-benzyl | —CH=C(CH$_3$)—CH=CH— | [(2α,4α)(B)] |
| 101 | B2 | 2-benzyl | —C(CH$_3$)=CH—C(CH$_3$)=CH— | [(2α,4α)(B)] |
| 102 | B2 | 2-benzyl | —CH=C(Cl)—CH=C(Cl)— | [(2α,4α)(B)] |
| 103 | B2 | 2-benzyl | —CH=C(CF$_3$)—CH=C(Cl)— | [(2α,4α)(B)] |
| 104 | B2 | 4-methyl | —CH=CH—S— | |
| 105 | B2 | 2-methylcyclohexyl | —CH=CH—CH=CH— | |
| 106 | B2 | 2-benzyl | —CH=CH—S— | [A(2α,4α)(B)] |
| 107 | B2 | 2-benzyl | —CH=CH—S— | [B(2α,4α)(B)] |
| 108 | B2 | 2-methylcyclohexyl | —CH=CH—S— | |

TABLE 3

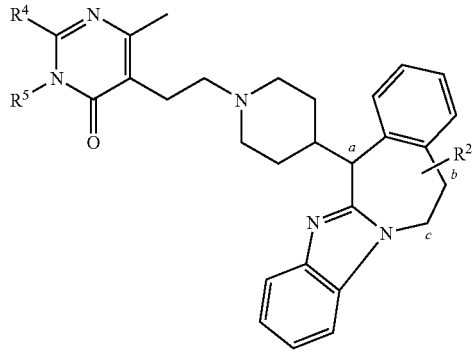

| Comp. nr | Ex. nr. | R² | R⁵ R⁴ | Phys. data and stereochemistry |
|---|---|---|---|---|
| 6 | B4 a) | —Me | —CH=CH—CH=CH— | hydrate (1:1) |
| 110 | B4 a) | —Me | —CH=CH—S— | |
| 111 | B4 a) | —CH$_2$—Phe | —CH=CH—CH=CH— | |

TABLE 3-continued

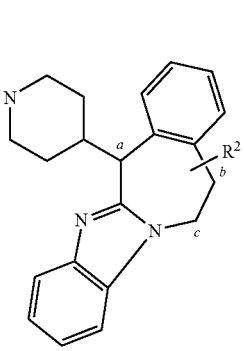

| Comp. nr | Ex. nr. | R² | R⁵ R⁴ | Phys. data and stereochemistry |
|---|---|---|---|---|
| 112 | B5 b) | —CH$_2$—Phe | —CH=CH—CH=CH— | |
| 7 | B5 b) | —CH$_2$—Phe | —CH=CH—S— | |
| 113 | B4 a) | —Phe | —CH=CH—S— | |

TABLE 4

| Co. nr. | Ex. nr. | R⁵ R⁴ | A B | C D | Phys. data and stereochemistry |
|---|---|---|---|---|---|
| 114 | B1 | —CH=CH—CH=CH— | —CH=CH—S— | —CH=CH—CH=CH— | H₂O(1:1) (E)-2-butenedioate(1:1) |
| 115 | B1 | —CH=CH—S— | —CH=CH—S— | —CH=CH—CH=CH— | H₂O(2:1) (E)-2-butenedioate(2:3) |
| 116 | B1 | —CH=CH—CH=CH— | —CH=CH—CH=CH— | —N=CH—CH=CH— | |
| 117 | B1 | —CH=CH—S— | —CH=CH—CH=CH— | —N=CH—CH=CH— | |
| 118 | B1 | —CH=CH—S— | —CH=CH—N(CH₃)— | —N=CH—CH=CH— | |

TABLE 5

| Co. nr. | Ex. nr. | R¹ | R² | R⁵ R⁴ | Phys. data and stereochemistry |
|---|---|---|---|---|---|
| 119 | B2 | 2-benzyl | H | —CH=CH—S— | cis |
| 3 | B2 | 2-benzyl | H | —CH=CH—S— | [(2a,4β)(B)] |
| 4 | B2 | 2-benzyl | H | —CH=CH—S— | trans |
| 120 | B2 | 2-benzyl | H | —CH=CH—CH=CH— | [(2a,4β)(B)] |
| 121 | B2 | 2-benzyl | H | —CH=CH—CH=CH— | [(2a,4β)(A)] |
| 122 | B2 | H | H | —CH₂—CH₂—CH₂—CH₂— | |
| 123 | B2 | H | H | —CH₂—CH₂—CH₂—S— | |
| 124 | B2 | H | H | —CH=CH—CH=CH— | |
| 125 | B2 | H | H | —CH₂—CH₂—S— | |
| 126 | B2 | H | H | —C(CH₃)=CH—S— | |
| 127 | B2 | H | H | —CH=C(CH₃)—CH=CH— | |
| 128 | B2 | H | H | —CH=CH—CH=C(CH₃)— | |
| 129 | B2 | H | H | —CH₂—C(CH₃)=N—N(CH₃)— | |
| 130 | B2 | H | H | —CH=CH—N(CH₃)— | |
| 131 | B2 | H | H | —CH=C(CH₃)—N(CH₃)— | |
| 132 | B2 | H | H | —O—C(CH₃)=CH— | (E)-2-butenedioate (1:2) |
| 133 | B2 | H | H | —C(CH₃)=N—N(CH₃)— | .H₂O(1:1) |
| 134 | B2 | 2-benzyl | H | —CH=CH—CH=CH— | [(2α,4α)(B)] |
| 135 | B2 | 2-benzyl | H | —CH=CH—CH=CH— | [(2α,4α)(A)] |
| 136 | B2 | H | H | —CH=CH—S— | .ethanedioate(2:5) .H₂O (2:1) |

TABLE 6

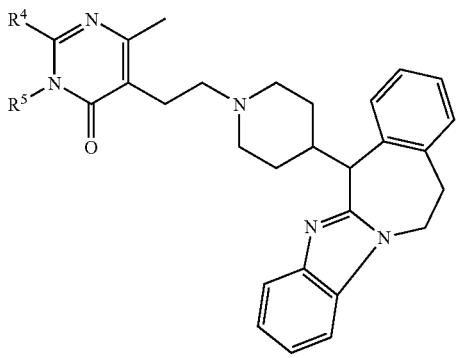

| Co. nr. | Ex. nr. | R⁵ R⁴ | Phys. data and stereochemistry |
|---|---|---|---|
| 5 | B3 | —CH—CH—S— | |
| 137 | B3 | —CH₂—CH₂—S— | |
| 138 | B3 | —CH₂—CH₂—CH₂—S— | |
| 139 | B3 | —CH═CH—CH═CH— | |

TABLE 7

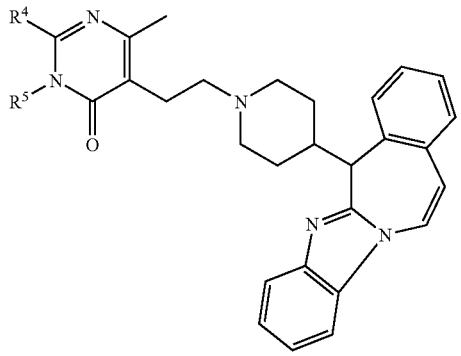

| Co. nr. | Ex. nr. | R⁵ R⁴ | Phys. data and stereochemistry |
|---|---|---|---|
| 140 | B6 | —CH═CH—CH═CH— | |
| 141 | B6 | —CH₂—CH₂—CH₂—S— | |
| 8 | B6 | —CH═CH—S— | |
| 142 | B6 | —CH₂—CH₂—S— | |

TABLE 8

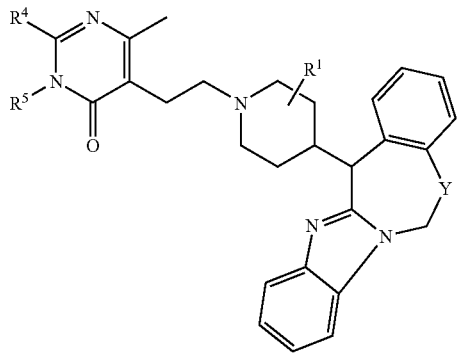

| Co. nr | Ex. nr. | Y | R¹ | R⁴ | R⁵ | Phys. data and stereochemistry |
|---|---|---|---|---|---|---|
| 143 | B2 | —CH₂—CH₂— | H | 2-pyridyl-CH₂-NH— | —CH₃ | |
| 144 | B1 | —CH₂—CH₂— | H | H₃C-O-CH₂CH₂-NH— | —CH₃ | |
| 145 | B1 | —CH₂—CH₂— | H | H₃C-CH₂CH₂CH₂-NH— | —CH₃ | .H₂O(1:1) |
| 146 | B1 | —CH₂—CH₂— | H | H₃C-CH₂-NH— | —CH₃ | |
| 150 | B1 | —CH₂—CH₂— | 2-benzyl | —NH₂ | —CH₃ | [(2α,4α)(B)] |
| 147 | B2 | —CH₂— | H | —NH₂ | —CH₃ | (Z)-2-Butenedioate (1:3).H₂O(1:1) |
| 148 | B2 | —CH₂— | H | H₃C-NH-C(O)-NH— | —CH₃ | |

TABLE 8-continued

| Co. nr | Ex. nr. | Y | R¹ | R⁴ | R⁵ | Phys. data and stereochemistry |
|---|---|---|---|---|---|---|
| 149 | B2 | —CH₂— | H | (benzamide N-methyl group) | —CH₃ | |
| 151 | B2 | —CH₂— | H | H₃C-CH₂-NH-CH₃ | —CH₃ | .HCl(1:3).H₂O(1:2) .2-propanolate(2:1) |

C. Pharmacological Examples

C1. In Vitro Determination of the Histaminic H1- and H2-Antagonist Activity.

Radioligand receptor binding studies were performed in vitro for radioligand binding of the selected compounds using a preparation of a tissue which was enriched in a particular receptor, i.e. the histamine H1- or H2-receptor. For the histamine H1-receptor, the tissue used were CHO-cells, permanently transfected with the human histamine H1-receptor. Only diphenhydramine was tested against guinea pig cells from the cerebral cortex. Competitive inhibition of [$^3$H] Pyrilamine by the tested compounds was conducted by incubating a low (nM) concentration of the radioligand with a small sample of the tissue preparation (0.2-5 ml; 1-5 mg tissue) in a buffered medium and various concentrations of the compounds, dissolved in DMSO, spanning at least 4 orders of magnitutude around the pIC$_{50}$ value, derived from the inhibition curve. The histaminic H2-antagonist activity was tested in much the same way as the histaminic H1-antagonist activity, using guinea pig striatum cells and [$^{125}$I]APT as the radioligand in a concentration of 0.1 nM. Incubation was done during 150 min at 22° C.

All compounds according to our invention showed a pIC$_{50}$ value of 5 or more for histaminic H1-antagonist activity. Several compounds showed a pIC$_{50}$ value of 6 or more for histaminic H1-antagonist activity. These compounds are listed in Table 9. Furthermore is observed that a commercially available typical histamine H1-antagonist (diphenhydramine) exhibits only a slightly higher histaminic H1-antagonist activity as the bulk of the compounds according to our invention. Furthermore is shown that the commercially available H2-antagonists (ranitidine and cimetidine) exhibit histamine H2-activities in the range of the (moderately high) H2-activities of the compounds according to our invention. A selection of the compounds in Table 9, including commercially available compounds, was also tested in in vivo experiments for their ability to reduce ICP.

TABLE 9

Results of the histamine H1- and H2-antagonist activity receptor model screening.

| Comp. nr | H1-antagonist activity (pIC$_{50}$) | H2-antagonist activity (pIC$_{50}$) |
|---|---|---|
| 14 | 7.6 | |
| 94 | 7.0 | |
| 104 | 7.0 | |
| 46 | 6.9 | |
| 110 | 6.9 | |
| 1 (also tested in vivo) | 6.7 | 6.0 |
| 6 | 6.7 | |
| 23 | 6.7 | |
| 78 | 6.7 | |
| 81 | 6.7 | |
| 82 | 6.7 | |
| 50 | 6.6 | |
| 55 | 6.6 | |
| 87 | 6.6 | |
| 12 | 6.5 | |
| 13 | 6.5 | |
| 15 (also tested in vivo) | 6.5 | |
| 45 (also tested in vivo) | 6.5 | |
| 48 | 6.5 | |
| 49 | 6.5 | |
| 53 | 6.5 | |
| 54 | 6.5 | |
| 83 | 6.5 | |

TABLE 9-continued

Results of the histamine H1- and H2-antagonist activity receptor model screening.

| Comp. nr | H1-antagonist activity (pIC$_{50}$) | H2-antagonist activity (pIC$_{50}$) |
|---|---|---|
| 88 | 6.5 | |
| 20 | 6.4 | |
| 32 (also tested in vivo) | 6.4 | |
| 47 (also tested in vivo) | 6.4 | |
| 57 | 6.4 | |
| 58 | 6.4 | |
| 105 | 6.4 | |
| 29 | 6.3 | |
| 51 | 6.3 | |
| 84 | 6.3 | |
| 17 (also tested in vivo) | 6.2 | |
| 27 | 6.2 | |
| 37 | 6.2 | |
| 2 (also tested in vivo) | 6.1 | |
| 30 (also tested in vivo) | 6.1 | |
| 35 | 6.1 | |
| 56 | 6.1 | |
| 89 | 6.1 | |
| 90 | 6.1 | |
| 9 (also tested in vivo) | 6.0 | |
| 31 | 6.0 | |
| 41 | 6.0 | |
| 44 (also tested in vivo) | 6.0 | |
| 102 | 6.0 | |
| Ranitidine (also tested in vivo) | — | 5.5 |
| Cimetidine | — | 5.9 |
| Diphenhydramine (also tested in vivo) | 7.2 | — |

C.2. In Vivo Pharmacology

Closed Head Injury (CHI) Model

A clinically relevant rat model for traumatic brain injury was used to test the compounds according to the invention and the commercially available compounds. This model mimics several clinical features of traumatic brain injury, such as increased ICP, decreased cerebral perfusion pressure, morphologic alterations including diffuse axonal injury, neuronal necrosis and contusion, impairment of autoregulation of cerebral blood flow and reduction of brain oxygenation and was applied for screening drugs with ICP-lowering effects. Trauma was induced in intubated, isoflurane anesthetized (1.5% isoflurane in a mixture of 30% $O_2$ and 70% $N_2O$) Sprague-Dawley rats (380-400 g) stereotaxically positioned on a table mounted on 4 springs. A 400 g steel cylinder, protected with a 9 mm diameter silicon disc, was dropped on the unprotected skull from a height of either 70 cm or 50 cm (respectively 'severe' and 'moderate' head injury). The impact area was centered between bregma and lamda. ICP was recorded using a Codman microsensor probe inserted in the parietal cortex. In both severe and moderate head injuries the ICP increased immediately after trauma and remained elevated for several days. The severe head injury mode was used for the evaluation of pharmacological effects immediately after trauma (screening procedure). When survival and recovery from anesthesia was envisaged, the moderate head injury mode was applied. In pharmacological studies, animals with a pathological ICP between 12.5 and 35 mm Hg were included. The changes in ICP, mean arterial blood pressure (MABP) and cerebral perfusion pressure CPP (=MABP—CPP) were expressed as percentage of the initial value at onset of the treatment.

Screening Procedure for the Compounds According to the Invention

On a weekly base, 4 treated groups of 3 rats were compared with 3 saline treated animals. Since conventional statistical methods require a larger amount of animals, a sequential procedure was used. Sequential methods operate in different stages. At each stage, a group of animals was selected as homogeneous as possible. Animals were randomly allocated to either drugs or saline. The procedure allowed to make the decision of rejecting the drug, accepting the drug as active or to continue with a new group of animals in a next stage. Given the biological relevant level of activity that must be detected, the expected fraction of false positive and negative results was known and fixed. A sequential two-sample grouped rank test was used. A three stage sequential design with a relatively small number of animals at each stage showed to be optimal. Despite the variability in the individual data, the procedure consistently accepted reference treatments such as mannitol as active, while controls were rejected. Clinically relevant i.v. doses of mannitol (3 g over 45 min) consistently reduced the ICP (mean reduction about 20%).

TABLE 10

Results of the screening procedure.

| Treatment[1] | Delta %[2] | Decision[3] |
|---|---|---|
| Compound 9 | −12.4 | active |
| Compound 15 | −23.3 | active |
| Compound 17 | −8.9 | active |
| Compound 30 | −9.3 | active |
| Compound 32 | −13.9 | active |
| Compound 44 | −14.8 | active |
| Compound 45 | −13.1 | active |
| Compound 47 | −12.0 | active |
| CD10% | 5.1 | not active |
| CD10% + 3H2T | 10.0 | not active |
| CD20% | 19.1 | not active |
| CD20% + HCl | 2.4 | not active |
| Mannitol[1] | −21.7 | active |
| Mannitol[2] | −22.1 | active |
| Mannitol[3] | −13.0 | active |
| Mannitol[4] | −19.3 | active |
| Mannitol[5] | −19.9 | active |

[1]Experimental compounds administered as a bolus of 1 mg/kg given in 1 min, followed by an infusion of 0.5 mg/kg/min for 44 min; solvents administered as a 0.4 ml bolus in 1 min followed by an infusion of 0.2 ml/min for 44 min; mannitol given as an infusion of 67 mg/kg/min for 45 min.

[2]Delta %: average change of the relative ICP from baseline over the treatment period.

[3]Decision: based upon sequential statistical evaluation.

CD = hydroxypropyl-β-cyclodextrin solvent

H2T = tartaric acid solvent

Mannitol[1-5]: Mannitol was evaluated 5 times in separate tests (positive controls). The result of each test is mentioned.

Further Studies

Table 11 shows the changes in some relevant physiological variables recorded during treatment after severe CHI in rats. Treatment was started at 20 min after severe head injury and involved administering a dose of 0.5 mg/kg/min during 10 minutes, followed by 0.1 mg/kg/min during 50 minutes.

TABLE 11

Changes in relevant physiological variables during treatment after severe CHI in rats.

| | Solvent (n = 10) | Compound 2 (n = 10) | Compound 1 (n = 10) | Racemate (comp. 1 and comp. 2) (n = 10) |
|---|---|---|---|---|
| ICP (%) | 1.6 (−9.4; 11.1) | −15.3 (−20.0; −9.5)* | −15.4 (−22.6; −11.5)* | −19.1 (−24.9; −10.8)* |
| MABP (%) | −1.2 (−2.7; 3.7) | 18.8 (−2.0; 31.0)* | −3.6 (−11.9; −1.5) | 0.6 (−5.1; 8.5) |
| CPP (%) | −1.3 (−8.0; 5.8) | 24.2 (0.9; 43.6)* | −1.9 (−8.9; 0.4) | 7.5 (−2.4; 15.5) |
| ETCO$_2$ (%) | 8.0 (−1.2; 12.9) | −4.4 (−8.9; 2.3)* | 2.2 (−0.8; 8.4) | 2.4 (−7.8; 3.8) |
| Heart rate(%) | −2.7 (−5.4; 3.9) | −9.6 (−21.8; 0.7) | −4.1 (−11.4; 1.9) | 5.6 (−11.7; 0.4) |
| Resp. rate(%) | 3.6 (−4.3; 11.8) | 6.6 (−1.3; 14.6) | 5.3 (−3.3; 13.6) | 9.6 (3.0; 14.8) |

Average change over the entire treatment period, expressed as % change of initial value.
Values are medians (95% C.I.).
*= Significantly different from solvent group (p < 0.05, Dunnett's test)
Solvent: 10% hydroxypropyl-beta-cyclodextrine, tartaric acid, NaOH and mannitol in pyrogen free water; pH = 4; osmolarity 312-314 mOsm/kg; compound concentration 2 mg/ml.
Compound: pyrimido[1,2-a]benzimidazol-4(10H)-one, 3-[2-[4-(11,12-dihydro-6H-benzimidazo[2,1-b][3]benzazepin-6-yl)-2-(phenylmethyl)-1-piperidinyl]ethyl]-2,10-dimethyl (E)-2-butenedioate (2:3) hydrate (1:1)
Compound 1: (B)[(2α, 4β)(A)]
Compound 2: (A)[(2α, 4β)(A)]
Racemate (comp. 1 and comp. 2): (2α, 4β)(A), i.e. the racemic mixture of Compound 1 and Compound 2
ICP: Intracranial pressure
MABP: Mean arterial blood pressure
CPP: Cerebral perfusion pressure
ETCO$_2$: End tidal CO$_2$ The significant effect of compound 2 on MABP is much less pronounced when the compound is given at a continuous infusion of 0.1 mg/kg.min. In this case a blood pressure peak is not present and increases in MABP larger than 20% are not observed (median MABP increase at the end of the infusion is 9%, n=6). The maximal reduction of ICP at this dose is comparable to the one observed when the infusion is preceded by the 'loading dose' of 5 mg/kg over 10 min, but the time required to obtain this effect is longer (median: 30 min).

Effect of Ranitidine and Dinhenhydramine on the ICP

Ranitidine was infused for 6 min at a dose of 2 mg/kg/min in the rat CHI-model after inflicting severe head injury. Solvent (NaCl+H2T) was given at the same rate. In each group, 6 rats were treated. Ranitidine was observed to yield a statistically significant larger reduction in ICP than in the solvent-treated group (7.7% versus 0.5% reduction, which was significant at p=0.013). The percentage of reduction are calculated as % change of the ICP recorded at the onset of the treatment and at the end of the infusion. No significant change in blood pressure was observed.

Diphenhydramine was infused for 10 min at a dose of 1 mg/kg/min in the rat CHI-model after inflicting severe head injury. Three rats were treated. Diphenhydramine was observed to yield a 34% reduction in ICP without any significant effect on the blood pressure.

Comparative Experiments with Agonists.

For comparison, two commercially available H2-agonists (dimaprit and impromidine) were also tested by infusion into non-traumatized rats, using a dose of 0.5 mg/kg/min for 10 minutes for dimaprit and increasing doses up to 3.75 mg/kg/hour for impromidine. No effects were observed. When dimaprit was dosed at the high dose of 2 mg/kg/min for 10 minutes, and impromidine was doses as a bolus of 0.5 mg/kg blood pressure and ICP were observed to drop, but recovered after the treatment.

It was therefor concluded that histamine H1-and/or H2-receptor antagonists exhibited the effect of lowering the ICP and having in the meantime hardly any significant effect on the blood pressure.

Experiments with Commercially Available H1- and H2-Antaponists

A number of commercially available H1- and H2-antagonists was infused for 10 min at a dose of 0.5 mg/kg/min in the rat CHI-model after inflicting severe head injury. Solvent (NaCl+H2T) was given at the same rate. In each group, 6 rats were treated. The results of the behavior of the ICP and BP in the first 15 minutes are summarized in Table 12.

TABLE 12

Effect of commercially available H1- and H2-antagonists.

| Compound | Effect on ICP | Effect on blood pressure |
|---|---|---|
| solvent | 0 | 0 |
| Cyclodextrine | − | + |
| Alimemazine | − | − |
| Antazoline | −− | −− |
| Brompheniramine | − | −− |
| Chlorcyclizine | − | 0 |
| Chlorpheniramine | − | + |
| Clemastine | − | −− |
| Clemizole | − | − |
| Cyproheptadine | −− | −− |
| Dimethindene | − | + |
| Diphenhydramine | −− | 0 |
| Diphenylpyraline | − | −/0 |
| Hydroxyzine | − | 0 |
| Ketotifen | −− | 0 |
| Loratidine | − | + |
| Niaprazine | −− | −− |
| Oxatomide | − | − |
| Pheniramine | −− | −− |
| Promethazine | − | + |
| Pyrilamine (see FIG. 5) | −− | 0 |
| Ritanserine | − | − |
| Tiotidine | −− | −/0 |
| Zolantidine | − | 0 |

0: no effect;
−: decrease;
−−: strong decrease;
+: increase

Dose Response for Compound 1

Results of a blinded, completely randomized study of the effect of a 10 min infusion of Compound 1 at different doses (0.125, 0.25, 0.5, 1 and 2 mg/kg/min) in the rat CHI model indicate that during treatment Compound 1 invokes a sustained dose-dependent decrease of ICP (FIG. 1). Starting at 1 mg/kg/min Compound 1 yields a statistically significant larger reduction in ICP than in the solvent-treated group. In the 10 min period following the infusion a highly significant dose-dependent effect on ICP remains present (FIG. 2).

Effects of Compound 2. Compound 1 and Racemate (Comp. 1 and Comp. 2) on Brain Hemoglobin Concentration and Oxygenation.

Near-infrared spectroscopy (NIRS) of the rat brain 'in vivo' allows to quantify non-invasively saturation of brain haemoglobin with oxygen (HbSat) and total brain haemoglobin concentration ([HbTot]). The latter is a measure for cerebral blood volume (CBV). Changes in the redox state of the mitochondrial enzyme cytochrome oxidase (CytOx), an indicator for tissue oxygenation, can also be monitored.

All compounds 2, 1 and the racemate (Comp. 1 and Comp. 2) do not have a significant effect on [HbTot] when given 24 h after moderate head injury at a i.v. dose of 0.5 mg/kg.min during 10 min, followed by 0.1 mg/kg.min during 45 min. Only compound 2 induces a small but statistically significant reduction of HbSat. HbSat is not affected by compound 1 and the racemate (Comp. 1 and Comp. 2). At the applied dose all compounds do not have an effect on the redox state of CytOx. These results indicate that in the applied experimental conditions a vasoconstrictive effect on cerebral blood vessels, if present, is limited and tissue oxygenation is not jeopardised.

Influence of Anaesthesia on the Effects of Compound 2

The effects of treatment with Compound 2 (i.v. infusion at a dose of 0.1 mg/kg.min during 30 min) at 24 h after moderate trauma were studied using different anesthetics (isoflurane, chloralhydrate, pentobarbital). When chloralhydrate (400 mg/kg i.p) is used as anesthetic, ICP decreases to 75% of initial value and MABP gradually increases to 110% of initial value (medians, n=6). These effects are comparable with those observed under isoflurane anesthesia. When pentobarbital (60 mg/kg i.p.) is used, Compound 2 induces a significant gradual increase in MABP up to 141% of initial value at the end of the infusion, whereas ICP decreases to 64% of initial value (medians, n=6). These results indicate that the same pattern of effects on ICP and MABP are observed under various types of anesthesia. The fact that the compound reduces the ICP significantly under pentobarbital anesthesia is important, as barbiturates are often applied in traumatic brain injury patients. Barbiturates also reduce the ICP and an important additional effect can be obtained with the compound.

The Effect of Repeated Application of Compound 1 and of Mannitol on Elevated ICP in Traumatized Rats.

Compound 1 was given 2 times with intermittent periods of 20 min at a i.v. dose of 1 mg/kg/min during 10 min, starting a first time 20 min after induction of severe head injury.

Mannitol was given i.v. in the same time windows as Compound 1 at a dose of 0.125 g/kg/min. The control animals received the solvent (containing 10% HP-β-CD, pH 4) only.

Infusion with Compound 1 results in rapid reduction of ICP (FIG. 3). This effect is amplified after termination of each infusion period. Blood pressure drops during Compound 1 treatment but is restored again after this episode. This is in contrast with mannitol, that induces a lowering of ICP and an increase in blood pressure during each infusion followed by a decrease in blood pressure after termination of each treatment. Only in the Compound 1—treated animals a clear dissociation between the changes in blood pressure and ICP can be observed. In contrast, the mannitol treated animals exhibit more or less parallel changes in blood pressure and intracranial pressure. This indicates that the pharmacological effect of Compound 1 is different from that of mannitol.

Effect of Compound 1 on Cold Lesion-Induced Rise of ICP in Rabbits

Cryo-lesions were induced in adult rabbits to obtain a pathological ICP that is caused by tissue oedema. A 8 mm stainless steel rod was placed at predetermined coordinates on the exposed skull of deeply anaesthetised rabbits and cooled for 10 min with liquid nitrogen. One day later the animals were re-anaesthetised and ICP and blood pressure continuously recorded as described for the rat. After a stabilisation period of 15 min, Compound 1 was infused for 10 min at a dose of 2 mg/kg/min. Solvent (preclinical formulation containing 10% HP-β-CD, pH 4) was given for 10 min at a rate of 2 ml/min.

During infusion of the Compound 1, the blood pressure drops and although there is no immediate decrease in ICP, the ICP rise that is observed in the solvent-treated animals tends to be antagonised (FIG. 4). When drug infusion is terminated, blood pressure comes back to the initial value and a significant ICP reduction is seen that persists during the entire recording period.

These results indicate that the compound reduces the ICP also in non-rodent species and in pathologic conditions different from closed head injury.

The Effect of Compound 1 and on ICP in Non-Traumatized Animals.

Rats The effect of Compound 2, Compound 1 and Racemate (comp. 1 and comp. 2) on ICP, MABP and CPP was tested in anaesthetised non-traumatised rats. The compounds were administered i.v. and the same dose was given as in traumatized rats (0.5 mg/kg/min during 10 minutes, followed by 0.1 mg/kg/min during 50 min). The results were comparable with those obtained in the traumatized animals.

Conclusion

The results obtained in traumatized animals, animals with cold lesion, and non-traumatized animals indicate that the compounds are active in various conditions, even in normal conditions. Their field of application probably includes various pathological conditions in which intracranial hypertension is present.

The invention claimed is:
1. A compound according to Formula (I)

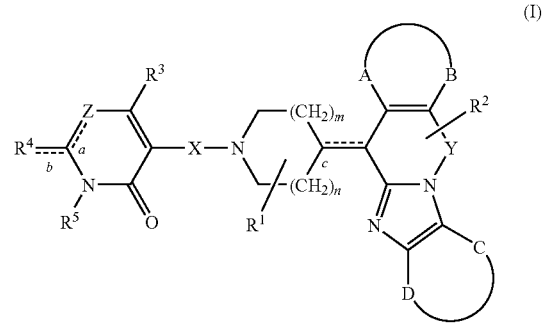

the pharmaceutically acceptable acid or base addition salts thereof, the stereochemically isomeric forms thereof and the N-oxide form thereof, wherein:

m is 1 or 2;
n is 0 or 1;
m+n must equal 2
a, b, c independently are a single or a double bond;
X is a covalent bond or a bivalent radical of a $C_{1-6}$ alkanediyl wherein one or more —$CH_2$— groups may be optionally replaced with —O—, —S—, —CO—, or $NR^7$— wherein:
  $R^7$ is hydrogen, alkyl, Ar, Ar-alkyl, Het, Het-alkyl, hydroxyalkyl, alkyloxy, alkyloxyalkyl, alkyloxyalkyloxyalkyl, aminoalkyl, mono- or dialkylaminoalkyl, formyl, alkylcarbonylaminoalkyl, alkylcarbonyloxyalkyl, alkyloxycarbonyl, alkyloxycarbonylalkyl, alkylaminocarbonyl, alkylaminocarbonylalkyl, hydroxyalkyloxyalkyl, aminocarbonyl, aminocarbonylalkyl, alkyloxycarbonyl or alkylcarbonyloxyalkyloxyalkyl;
Y is —$CH_2$—$CH_2$—,
Z is N, in which case a is a double bond and b is a single bond or N—$R^7$ in which case a is a single bond, b is a double bond and $R^7$ is defined as above;
$R^1$, $R^2$ independently are hydrogen, hydroxy, alkyl, alkyloxy, Ar, Ar-alkyl, di(Ar-)alkyl, Het or Het-alkyl;
—A—B- independently is a bivalent radical of formula —E—$CR^8$=$CR^8$— (a-1);

—$CR^8$=$CR^8$—E— (a-2);

—$CR^8$=$CR^8$—$CR^8$=$CR^8$— (a-3);

wherein
$R^8$ each independently is hydrogen, halo, hydroxy, alkyl or alkyloxy;
E is a bivalent radical of formula —O—, —S— or— $NR^7$- wherein $R^7$ is defined as above;
—C—D— independently is a bivalent radical of formula —$CR^8$=$CR^8$—$CR^8$=$CR^8$— (b-1);

—N=$CR^8$—$CR^8$=$CR^8$— (b-2);

—$CR^8$=N—$CR^8$=$CR^8$— (b-3);

—$CR^8$=$CR^8$—N=$CR^8$— (b-4);

—$CR^8$=$CR^8$—$CR^8$=N— (b-5);

wherein $R^8$ is defined as above;
$R^3$ is hydrogen, halo, hydroxy, alkyl, alkyloxy, Ar, Ar-alkyl, di(Ar-)alkyl, Het or Het-alkyl;
$R^4$ is hydrogen, alkyl, amino, alkylamino, Ar-amino, Het-amino, alkylcarbonylamino, Ar-carbonylamino, Het-carbonylamino, alkylaminocarbonylamino, Ar-aminocarbonylamino, Het-aminocarbonylamino, alkyloxyalkylamino, Ar-oxyalkylamino or Het-oxyalkylamino;
$R^5$ is hydrogen or alkyl;
  or $R^4$ and $R^5$ together may form a bivalent radical of Formula —M—$CR^9$=$CR^{10}$— (c-1);

—$CR^{10}$=$CR^9$—M— (c-2);

—M—$CR^9R^8$—$CR^{10}R^8$— (c3);

—$CR^{10}R^8$—$CR^9R^8$—M— (c-4);

—$CR^8$=N—$NR^7$— (c-5);

—$NR^7$—N=$CR^8$— (c-6);

—$CR^8$=$CR^9$—$CR^{10}$=$CR^8$— (c-7);

—$CR^8R^8$—$CR^9R^8$—$CR^{10}R^8$—M— (c-8);

—M—$CR^{10}R^8$—$CR^9R^8$—$CR^8R^8$— (c-9);

—$CR^8R^8$—$CR^8$=N—$NR^7$— (c-10);

—$NR^7$—N=$CR^8$—$CR^8R^8$— (c-11);

wherein
$R^7$ and $R^8$ are defined as above;
$R^9$, $R^{10}$ independently are hydrogen, alkyl, halo, haloalkyl; or $R^9$ and $R^{10}$ together may form a bivalent radical of formula —$CR^8$=$CR^8$—$CR^8$=$CR^8$—; and
M is a bivalent radical of formula —$CH_2$—, —O—, —S— or —$NR^7$— wherein $R^7$ is defined as above;
Ar is a homocycle selected from the group of naphthyl and phenyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl and mono- or dialkylaminocarbonyl;
Het is a monocyclic heterocycle selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl and benzothienyl ; each monocyclic and bicyclic heterocycle may optionally be substituted on a carbon atom with halo, hydroxy, alkyl or alkyloxy;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;
halo is a substituent selected from the group of fluoro, chloro, bromo and iodo;
haloalkyl is a straight or branched saturated hydrocarbon radical having from 1 to 6 carbon atoms or a cyclic saturated hydrocarbon radical having from 3 to 6 carbon atoms, wherein one or more of any member of either group of said carbon atoms are substituted with one or more halo-atoms.

2. A compound according to claim 1, characterized in that, independently of each other, Ar is a naphthyl or phenyl, each optionally substituted with 1 substituent, each substituent independently selected from the group of halo or alkyl, Het is pyridinyl, pyrazinyl or indolyl, alkyl is methyl, ethyl or cyclohexylmethyl, halo is fluoro or chloro and haloalkyl is trifluoromethyl.

3. A compound according to claim 1, characterized in that —A—B—is a bivalent radical of formula (a-1) or (a-3), wherein E is a bivalent radical of formula - O, —S— or —$NR^7$— wherein $R^7$ is hydrogen, $R^8$ is hydrogen, —C—D— is a bivalent radical of formula (b-1) or (b-2), wherein $R^8$ is hydrogen and Y is a bivalent radical of formula $CH_2$—$CH_2$—.

4. A compound according to claim 1 characterized in that m and n are both 1.

5. A compound according to claim 1 characterized in that $R^1$ and $R^2$, each independently are hydrogen, alkyl, Ar-alkyl, Het or Het-alkyl.

6. A compound according to claim 1 characterized in that X is a bivalent radical of formula —$CH_2CH_2$— or —$CH_2CH_2CH_2$—.

7. A compound according to claim 1 characterized in that $R^3$ is hydrogen or alkyl, Z is N—$R^7$ wherein $R^7$ is hydrogen or alkyl, a is a single bond and b is a double bond, and $R^4$ and $R^5$ together form a bivalent radical of Formula (c-1), (c-3), (c-5), (c-7), (c-8) or (c-10) wherein $R^7$ and $R^8$ are hydrogen.

8. A compound according to claim 7 characterized in that $R^9$ and $R^{10}$ together form a bivalent radical of formula -$CR^8$=$CR^8$-$CR^8$=$CR^8$- wherein R is hydrogen.

\* \* \* \* \*